(12) United States Patent
Kato et al.

(10) Patent No.: US 8,148,421 B2
(45) Date of Patent: Apr. 3, 2012

(54) PHENYLACETIC ACID DERIVATIVE

(75) Inventors: Hideo Kato, Fukui (JP); Osamu Nagata, Fukui (JP); Yoshiyuki Iwabuchi, Saitama (JP); Takahiro Sato, Tokyo (JP); Junichiro Uda, Saitama (JP); Tutomu Inoue, Chiba (JP); Hiroshi Nakamura, Chiba (JP); Nobuhide Kawasaki, Saitama (JP); Ippei Tanaka, Saitama (JP); Naoki Kurita, Ibaraki (JP); Tomohiko Ishikawa, Saitama (JP)

(73) Assignee: Fuji Yakuhin Co., Ltd., Saitama (JP)

( * ) Notice: Subject to any disclaimer, the term of this patent is extended or adjusted under 35 U.S.C. 154(b) by 353 days.

(21) Appl. No.: 12/440,540

(22) PCT Filed: Sep. 10, 2007

(86) PCT No.: PCT/JP2007/067568
§ 371 (c)(1),
(2), (4) Date: Aug. 12, 2009

(87) PCT Pub. No.: WO2008/032665
PCT Pub. Date: Mar. 20, 2008

(65) Prior Publication Data
US 2010/0048666 A1 Feb. 25, 2010

(30) Foreign Application Priority Data
Sep. 11, 2006 (JP) ................. 2006-245194

(51) Int. Cl.
*A61K 31/382* (2006.01)
*C07D 335/02* (2006.01)
(52) U.S. Cl. .......................... 514/432; 549/28
(58) Field of Classification Search .................. 514/432; 549/28
See application file for complete search history.

(56) References Cited

U.S. PATENT DOCUMENTS

| | | | |
|---|---|---|---|
| 4,461,912 | A | 7/1984 | Terada et al. |
| 5,434,292 | A | 7/1995 | Saita et al. |
| 6,627,656 | B2 | 9/2003 | Gallant et al. |
| 6,730,687 | B1 | 5/2004 | Miyachi et al. |
| 2001/0054008 | A1 | 12/2001 | Miller et al. |
| 2004/0214872 | A1 | 10/2004 | Suto et al. |

FOREIGN PATENT DOCUMENTS

| | | |
|---|---|---|
| EP | 641760 A1 | 4/1992 |
| EP | 1213287 | 6/2002 |
| GB | 2002762 | 2/1979 |
| GB | 1580113 | 11/1980 |
| JP | 54-061159 | 5/1979 |
| JP | 54-081260 | 6/1979 |
| JP | 56-049376 | 5/1981 |
| JP | 58-105939 | 6/1983 |
| JP | 5-132478 | 5/1993 |
| JP | 05-132478 | 5/1993 |
| JP | 2003-531194 | 10/2003 |
| WO | 93/02999 | 2/1993 |
| WO | 01/81312 | 11/2001 |
| WO | 2004/028535 | 4/2004 |

OTHER PUBLICATIONS

Singapore Search Report and Written Opinion dated Nov. 23, 2010 that issued with respect to patent family member Singapore Patent Application No. 200901827-6.
Abrams, P. et al. Neurourol. Urodyn., (2002) vol. 21, No. 2, p. 167-178.
Cardozo, L.D. et al., British Medical Journal, (1980) vol. 280, p. 281-282.
Palmer, J., Journal of International Medical Research, (1983) vol. 11, Suppl. 2, p. 11-17.
Al-Waili, N., Clinical and Experimental Pharmacology & Physiology, 13, pp. 139-142, 1986.
Al-Waili, N., Journal of Urology, 142, pp. 1290-1292, 1989.
Flamant, G., La Presse Medicale, 24, pp. 31-34, 1995.
BJU International, 88, pp. 126-127, 2001.
Abstracts of the general meeting in the 90th convention of the Japanese Urological Association (2002) pp. 585, Journal of Japanese Urological Association, 93, p. 394, 2002. Abstracts of the 24th annual meeting of the Japanese Society of Clinical Pharmacology and Therapeutics (2003), Japanese Journal of Clinical Pharmacology and Therapeutics, 35, 175S, 2004.
Acta Medica Okayama, 58, pp. 45-49, 2004.
Oyo Yakuri (Applied Pharmacology), 21, pp. 753-771, 1981.
Yakuri to Chiryo (Japanese Pharmacology & Therapeutics, 14, pp. 5191-5209, 1986.
Search report from E.P.O. that issued with respect to patent family member European Patent Application No. 07828211 8, mailed Oct. 7, 2011.

*Primary Examiner* — Taofiq A Solola
(74) *Attorney, Agent, or Firm* — Greenblum & Bernstein, PLC

(57) ABSTRACT

A compound represented by the formula (1) or a salt thereof (--- represents a single bond, or a double bond; $R^1$ represents hydrogen atom, or an alkyl group; $R^2$ and $R^3$ represent hydrogen atom, or an alkyl group; $R^4$ and $R^5$ represent hydrogen atom, hydroxy group, an alkoxyl group, a halogen atom, or a mono- or di-alkyl-substituted amino group; $R^6$ represents hydrogen atom, cyano group, an alkoxycarbonyl group, or carboxy group; $R^7$ represents one or two of substituents on the benzene ring (the substituents are selected from hydrogen atom, a halogen atom, nitro group, cyano group, hydroxy group, amino group, an alkyl group, and an alkoxyl group); A represents a 5-membered or 6-membered non-aromatic heterocyclic ring containing one or two contiguous sulfur atoms (the sulfur atoms may independently form oxide); W --- represents oxo group, hydrogen atom, an alkyl group, hydroxy group, an alkoxyl group, or a halogen atom; and X represents oxygen atom, or sulfur atom), or a salt thereof, which has a superior suppressing action against prostaglandin $E_2$ production and is useful as an active ingredient of medicaments with reduced adverse reactions such as gastrointestinal disorders.

(1)

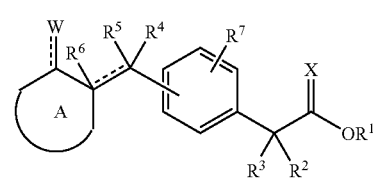

3 Claims, No Drawings

PHENYLACETIC ACID DERIVATIVE

TECHNICAL FIELD

The present invention relates to a novel phenylacetic acid derivative having a superior suppressing action against prostaglandin-$E_2$ production and useful as an active ingredient of medicaments with reduced adverse reactions such as gastrointestinal disorders.

BACKGROUND ART

Urinary urgency with intolerable uresiesthesia significantly limits the quality of life (QOL). It is known that patients with pollakiuria (i.e. urinary frequency) accompanied by urinary urgency are very frequent among patients complaining dysuria. Although pathological causes thereof have not been fully elucidated, it is considered that neurogenic or non-neurogenic detrusor (bladder smooth muscle) overactivity constitutes common background. Recently, overactive bladder (OAB) is defined as "urgency, with or without urge incontinence, usually with frequency and nocturia." by the International Continence Society (Neurourol. Urodyn., 2002). Recently, According to the definition, OAB represents those symptoms expressed by overactivity of detrusor, which does not necessarily need diagnosis based on a uroflometry test, and is understood as a syndrome accompanied by one or more of the symptoms mentioned above in addition to urinary urgency.

As therapeutic agents for OAB, muscarinic acetylcholine receptor antagonists (anticholinergic drugs) have so far been mainly developed and clinically applied. However, it is considered that they do not fully satisfy medical needs, because their effects per se are not sufficient, and moreover, adverse reactions deriving from the anticholinergic action such as mouth dryness and constipation are not satisfactorily eliminated.

Therapeutic agents for OAB, having a completely different mode of action from that of the anticholinergic drugs, have also been researched. It is suggested that prostaglandin $E_2$ ($PGE_2$) constricts the bladder smooth muscle itself through the EP1 receptor, and also acts on the sensory nerve as an afferent nerve system in the bladder to accelerate urination reflex, and thereby induce pollakiuria. A so-called hyperesthetic state is involved in the expression of urinary urgency, and one of examples of the causes of hyperesthesia in OAB or interstitial cystitis is involvement of urinary tract epithelium in excitatory regulation of sensory nerve terminals. Various substances such as adenosine triphosphate (ATP), PG, acetylcholine, tachykinin, vasoactive intestinal peptide (VIP), and nitric oxide (NO) are released form the urinary tract epithelium, and it is believed that PG especially has effects on the excitability of sensory nerve terminals to cause hyperesthesia. Therefore, a curative effect for OAB is expected for $PGE_2$ production suppressors.

It is already known that, for example, cyclooxygenase (COX) inhibitors having a PG production suppressing action such as acetylsalicylic acid (aspirin, salicylic acid type antiinflammatory agent), indomethacin (indoleacetic acid type antiinflammatory agent), flurbiprofen (propionic acid type antiinflammatory agent), ibuprofen (propionic acid type antiinflammatory agent), mefenamic acid (fenum type antiinflammatory agent), and diclofenac (phenylacetic acid type antiinflammatory agent), i.e., nonsteroidal antiinflammatory drugs (NSAIDs), have a pollakiuria improving effect (British Medical Journal, 2, pp. 281-282, 1980; Journal of International Medical Research, 11, pp. 11-17, 1983; Clinical and Experimental Pharmacology & Physiology, 13, pp. 139-142, 1986; Journal of Urology, 142, pp. 1290-1292, 1989; Presse Medicale, 24, pp. 31-34, 1995; BJU International, 88, pp. 126-127, 2000). The article in British Medical Journal (1980) mentioned above describes that "oncoming prostaglandin synthesis inhibitors will be more potent, and accordingly, they will be more effective also for unstable bladder."

It was also reported that loxoprofen (propionic acid type antiinflammatory agent), which is one of the antipyretic analgesics currently most widely used in Japan, was also effective for nocturia patients (Abstracts of the general meeting in the 90th convention of the Japanese Urological Association (2002) PP-585, Journal of Japanese Urological Association, 93, p. 394, 2002; Abstracts of the 24th annual meeting of the Japanese Society of Clinical Pharmacology and Therapeutics (2003), Japanese Journal of Clinical Pharmacology and Therapeutics, 35, 175S, 2004; Acta Medica Okayama, 58, pp. 45-49, 2004; U.S. Patent Published Application US2004/0054008).

Since NSAIDs including the medicaments mentioned above have modes of action different from that of the anticholinergic drugs, the adverse reactions caused by the anticholinergic action, such as mouth dryness and constipation observed for the anticholinergic drugs, can be avoided. However, available NSAIDs have damaging action on gastrointestinal tract (haemorrhage of digestive tract, ulcer, epigastric distress, abdominal pain, nausea and emesis, anorexia, stomatitis and the like), and the medicaments, including loxoprofen considered to have relatively weak damaging action (Oyo Yakuri (Applied Pharmacology), 21, pp. 753-771, 1981; Yakuri to Chiryo (Japanese Pharmacology & Therapeutics, 14, pp. 5191-5209, 1986), are recommended to be carefully used. Therefore, therapeutic agents for OAB having higher efficacy with superior safety have been desired.

[Non-patent document 1] Neurourol. Urodyn., 21, pp. 167-178, 2002
[Non-patent document 2] British Medical Journal, 2, pp. 281-282, 1980
[Non-patent document 3] Journal of International Medical Research, 11, pp. 11-17, 1983
[Non-patent document 4] Clinical and Experimental Pharmacology & Physiology, 13, pp. 139-142, 1986
[Non-patent document 5] Journal of Urology, 142, pp. 1290-1292, 1989
[Non-patent document 6] Presse Medicale, 24, pp. 31-34, 1995
[Non-patent document 7] BJU International, 88, pp. 126-127, 2000
[Non-patent document 8] Abstracts of the general meeting in the 90th convention of the Japanese Urological Association (2002) PP-585, Journal of Japanese Urological Association, 93, p. 394, 2002
[Non-patent document 9] Abstracts of the 24th annual meeting of the Japanese Society of Clinical Pharmacology and Therapeutics (2003), Japanese Journal of Clinical Pharmacology and Therapeutics, 35, 175S, 2004
[Non-patent document 10] Acta Medica Okayama, 58, pp. 45-49, 2004
[Patent document 1] U.S. Patent Published Application US2004/0054008

DISCLOSURE OF THE INVENTION

Object to be Achieved by the Invention

An object of the present invention is to provide a phenylacetic acid derivative having superior inhibitory action against prostaglandin-$E_2$ production and useful as a safe active ingredient of medicaments with reduced adverse reactions such as gastrointestinal disorders. The object of the present invention is, in particular, to provide a phenylacetic acid derivative useful as an active ingredient of medicaments having high effectiveness for prophylactic and/or therapeutic treatment of overactive bladder (OAB) with reduced adverse reactions such as gastrointestinal disorders.

Means for Achieving the Object

The inventors of the present invention conducted various researches to achieve the aforementioned object. As a result, they found that novel phenylacetic acid derivatives represented by the following general formula (1) had a potent suppressing action against $PGE_2$ production, and that they were useful as active ingredients of highly safe medicaments with reduced gastrointestinal disorders. The present invention was achieved on the basis of the findings.

The present invention thus provides a phenylacetic acid derivative represented by the following general formula (1), a salt thereof, or a hydrate or solvate thereof:

[Formula 1]

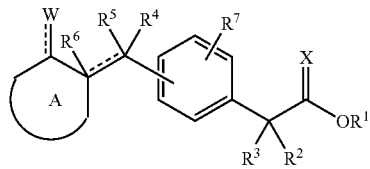

(1)

wherein ≕ represents a single bond, or a double bond; $R^1$ represents hydrogen atom, or a $C_{1-6}$ alkyl group; $R^2$ and $R^3$ independently represent hydrogen atom, or a $C_{1-6}$ alkyl group; $R^4$ and $R^5$ independently represent hydrogen atom, hydroxy group, a $C_{1-6}$ alkoxyl group, a halogen atom, or a mono- or di-($C_{1-6}$ alkyl)-substituted amino group; $R^6$ represents hydrogen atom, cyano group, a $C_{1-6}$ alkoxycarbonyl group, or carboxy group, provided that when ≕ in > $C(R^6)$≕$C(R^5)(R^4)$— represents a double bond, $R^4$ and $R^6$ do not exist; $R^7$ is one or two of the same or different substituents on the benzene ring selected from the group consisting of hydrogen atom, a halogen atom, nitro group, cyano group, hydroxy group, amino group, a $C_{1-6}$ alkyl group, and a $C_{1-6}$ alkoxyl group; A represents a 5-membered or 6-membered non-aromatic heterocyclic ring containing one or two contiguous sulfur atoms (the sulfur atoms may independently form oxide); W≕ represents oxo group, or W≕ represents two of the same or different substituents selected from the group consisting of hydrogen atom, a $C_{1-6}$ alkyl group, hydroxy group, a $C_{1-6}$ alkoxyl group, and a halogen atom; and X represents oxygen atom, or sulfur atom.

According to a preferred embodiment of the aforementioned invention, there is provided the aforementioned compound, a salt thereof, or a hydrate or solvate thereof, wherein $R^2$ is hydrogen atom, $R^3$ is hydrogen atom, or a $C_{1-6}$ alkyl group, both $R^4$ and $R^5$ are hydrogen atoms, or ≕in >$C(R^6)$ ≕$C(R^5)(R^4)$— is a double bond, or $R^4$ is hydrogen atom, and $R^5$ is hydroxy group, or a halogen atom, $R^6$ is hydrogen atom, or cyano group, $R^7$ is one or two substituents selected from the group consisting of hydrogen atom, a halogen atom, nitro group, and a $C_{1-6}$ alkoxyl group, A is a 5-membered or 6-membered non-aromatic heterocyclic ring containing one sulfur atom (the sulfur atom may form oxide), and W≕ is oxo group, two hydrogen atoms, two fluorine atoms, or a combination of hydrogen atom and hydroxy group.

From another aspect, the present invention provides a medicament comprising a substance selected from the group consisting of a compound represented by the aforementioned general formula (1), a salt thereof, and a hydrate or a solvate thereof as an active ingredient. The aforementioned medicament can be used for prophylactic and/or therapeutic treatment of various kinds of inflammatory diseases as a suppressor against $PGE_2$ production, and can also be used for prophylactic and/or therapeutic treatment of overactive bladder and the like.

From a still further aspect, the present invention provides a suppressor against $PGE_2$ production comprising a substance selected from the group consisting of a compound represented by the aforementioned general formula (1), a salt thereof, and a hydrate or a solvate thereof as an active ingredient.

The present invention further provides use of a substance selected from the group consisting of a compound represented by the aforementioned general formula (1), a salt thereof, and a hydrate or a solvate thereof for the manufacture of the aforementioned medicament or the aforementioned suppressor against $PGE_2$ production, a method for prophylactic and/or therapeutic treatment of an inflammatory disease, which comprises the step of administering a prophylactically and/or therapeutically effective amount of a substance selected from the group consisting of a compound represented by the aforementioned general formula (1), a salt thereof, and a hydrate or a solvate thereof to a mammal including human, and a method for suppressing the production of $PGE_2$ in a living body of a mammal including human, which comprises the step of administering an effective amount of a substance selected from the group consisting of a compound represented by the aforementioned general formula (1), a salt thereof, and a hydrate or a solvate thereof to the mammal including human.

Effect of the Invention

The compounds of the present invention represented by the aforementioned general formula (1) and salts thereof have a potent suppressing action against $PGE_2$ production, and have significantly reduced adverse reactions such as gastrointestinal disorders compared with the conventional non-steroid type antiinflammatory agents. Therefore, a medicament comprising the compound of the present invention or a salt thereof as an active ingredient is extremely useful as an active ingredient of a medicament for prophylactic and/or therapeutic treatment of various kinds of inflammatory diseases, overactive bladder, and the like.

BEST MODE FOR CARRYING OUT THE INVENTION

In the specification, the "alkyl group" may be any of straight, branched and cyclic alkyl groups and an alkyl group consisting of a combination thereof, and preferably a straight or branched alkyl group. The same shall apply to alkyl moieties of the substituents having an alkyl moiety (alkoxyl group, alkoxycarbonyl group, mono- or di-($C_{1-6}$ alkyl)-substituted amino group and the like).

Examples of the $C_{1-6}$ alkyl group include, for example, methyl group, ethyl group, n-propyl group, isopropyl group, n-butyl group, isobutyl group, s-butyl group, t-butyl group, n-pentyl group, n-hexyl group, and the like.

Examples of the $C_{1-6}$ alkoxyl group include, for example, methoxy group, ethoxy group, n-propoxy group, isopropoxy group, n-butoxy group, isobutoxy group, s-butoxy group, t-butoxy group, n-pentoxy group, n-hexoxy group, and the like.

Examples of the mono- or di-(lower alkyl)-substituted amino group include, for example, methylamino group, ethylamino group, dimethylamino group, diethylamino group, and the like.

Examples of the "halogen atom" include fluorine, chlorine, bromine, and iodine.

Although $R^2$ and $R^3$ independently represent hydrogen atom, or a $C_{1-6}$ alkyl group, it is preferred that both $R^2$ and $R^3$ are hydrogen atoms, or $R^2$ is hydrogen atom, and $R^3$ is a $C_{1-6}$ alkyl group, and it is more preferred that $R^2$ is hydrogen atom, and $R^3$ is a $C_{1-6}$ alkyl group.

When ---- in $>C(R^6)----C(R^5)(R^4)-$ is a single bond, it is preferred that all of $R^4$, $R^5$, and $R^6$ are hydrogen atoms, or $R^4$ and $R^6$ are hydrogen atoms, and $R^5$ is hydroxy group or a halogen atom, and it is more preferred that all of $R^4$, $R^5$, and $R^6$ are hydrogen atoms.

When ---- in $>C(R^6)----C(R^5)(R^4)-$ is a double bond, it is preferred that $R^4$ and $R^6$ do not exist, and $R^5$ is hydrogen atom.

Symbol "A" represents a 5-membered or 6-membered non-aromatic ring containing one or two contiguous sulfur atoms (the sulfur atoms may independently form oxide). Examples include, for example, tetrahydrothiophene, dihydrothiophene, dihydrothiopyrane (thiacyclohexene), tetrahydrothiopyrane (thiacyclohexane), and the like, but are not limited to the mentioned above.

The existing position of $R^7$ on the benzene ring is not particularly limited. One or two of the same or different substituents represented by $R^7$ may exist at arbitrary substitutable positions. $R^7$ preferably represents one or two substituents selected from the group consisting of hydrogen atom, a halogen atom, nitro group, and a $C_{1-6}$ alkoxyl group. Further, the existing position of $A>C(R^6)----C(R^5)(R^4)-$ binding to the benzene ring is not particularly limited, and may exist at an arbitrary substitutable position. The group is preferably binds at the para-position with respect to $-C(R^2)(R^3)-C(=X)-OR^1$.

W ---- is preferably oxo group, two hydrogen atoms, two fluorine atoms, or a combination of hydrogen atom and hydroxy group, more preferably oxo group, or a combination of hydrogen atom and hydroxy group. X is preferably sulfur atom or oxygen atom, more preferably oxygen atom.

As for the compounds of the present invention, geometrical isomers or tautomers based on a double bond may exist, and/or enantiomers or diastereoisomers may exist due to the presence of one or two or more asymmetric carbon atoms. Any of the aforementioned isomers in pure forms, arbitrary mixtures of the aforementioned isomers, racemates and the like fall within the scope of the present invention. Further, the compounds of the present invention may form a base addition salt or an acid addition salt depending on a type of substituent. A type of the salt is not particularly limited, and examples include, for example, metal salts such as sodium salts, potassium salts, and calcium salts, base addition salts such as ammonium salts, and organic amine salts, mineral acid salts such as hydrochlorides, sulfates, and nitrates, organic acid salts such as p-toluenesulfonates, methanesulfonates, tartrates, and maleates, and the like. However, the salt is not limited to these examples. Further, the compounds of the present invention in a free form or the form of an acid may exist as a hydrate or a solvate, and these substances also fall within the scope of the present invention. Examples of the hydrate include, for example, ½ hydrates, monohydrates, dihydrates, and the like, but the hydrate is not limited to these examples. Type of a solvent that forms the solvate is not particularly limited, and examples include ethanol, ethyl acetate, tetrahydrofuran, dioxane and the like. However, the solvent is not limited to these examples.

Although the method for preparing the compounds of the present invention is not particularly limited, they can be prepared by, for example, the following preparation methods. In these methods, it may sometimes be advantageous for the preparation to introduce an appropriate protective group to a functional group in a starting material or intermediate depending on the type of the functional group. Examples of such a functional group include amino group, hydroxy group, carboxy group and the like. When the preparation is performed by introducing a protective group into a functional group, a desired compound can be obtained by appropriately removing the protective group in any of the preparation stages. Examples of the type of such a protective group and methods for introduction and deprotection thereof include those described in, for example, Greene and Wuts, "Protective Groups in Organic Synthesis (Third Edition)", and the like.

<Preparation Method 1>

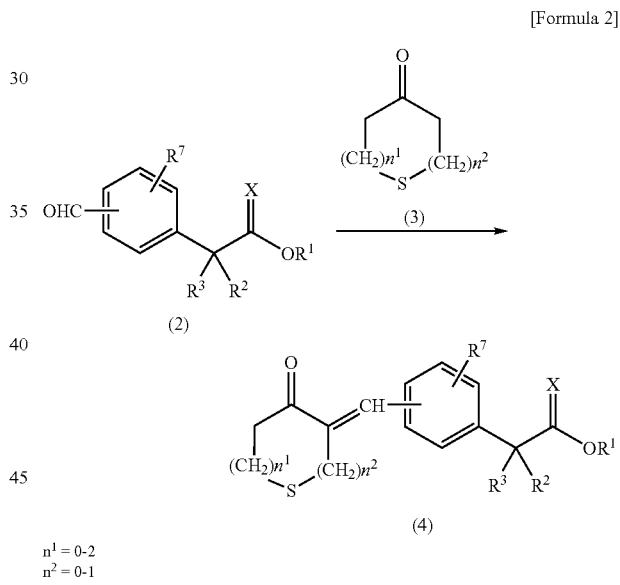

[Formula 2]

$n^1 = 0-2$
$n^2 = 0-1$ (In the formula, $n^1$ represents an integer of 0 to 2 (when $n^1$ is 0, it means that the methylene represented by $(CH_2)n^1$ does not exist), $n^2$ represents 0 or 1 (when $n^2$ is 0, it means that the methylene represented by $(CH_2)n^2$ does not exist), the other symbols have the same meanings as those defined above, and the same shall apply to the following descriptions.)

The compounds represented by the general formula (4) can be obtained by dehydration condensation of a substituted benzaldehyde represented by the general formula (2) and a compound represented by the general formula (3) in an amount corresponding to the reaction. Although this reaction can be performed without solvent, the reaction may be performed in an organic solvent such as tetrahydrofuran, dioxane, toluene, methanol, ethanol, and ethyl acetate. The reaction can be performed at a temperature of from room temperature to a temperature under reflux by heating with stirring, and a base and/or an acid may be added for the purpose of promoting the reaction as the case may be. Examples of the base include, for example, piperidine, sodium hydroxide, and the like, and examples of the acid include hydrochloric acid, sulfuric acid, acetic acid, p-toluenesulfonic acid, and the like.

<Preparation Method 2> general formula (7). For example, they can be prepared by a method of reducing a compound represented by the general formula (7) with a reducing agent (for example, magnesium, sodium amalgam and the like) in an amount corresponding to the reaction in a solvent such as tetrahydrofuran, dioxane, methanol, ethanol, water, acetic acid, or a mixed solvent

[Formula 3]

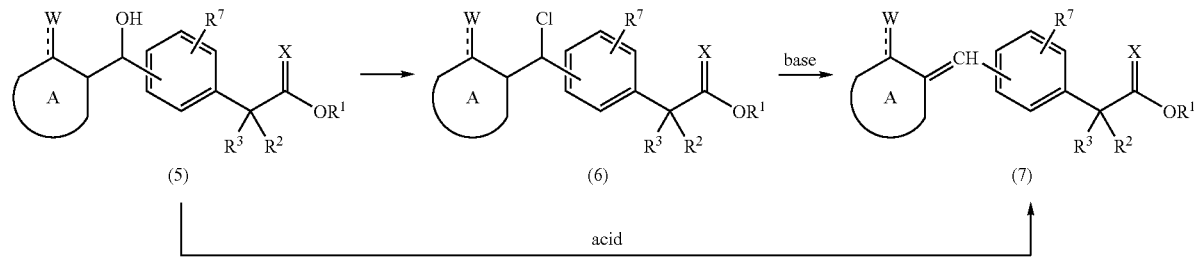

The compounds represented by the general formula (6) can be prepared by reacting a compound represented by the general formula (5) with a halogenating agent in an amount corresponding to the reaction in an organic solvent at a temperature of from room temperature to a temperature under reflux by heating. Examples of the organic solvent include, for example, chloroform, carbon tetrachloride, benzene, dioxane, and the like. Examples of the halogenating agent include thionyl chloride, phosphorus pentachloride and the like. The compounds represented by the general formula (7) can be obtained by subjecting a compound represented by the general formula (6) to a leaving reaction. For example, a target compound can be obtained by reacting the compound at a temperature of from room temperature to a temperature under reflux by heating in an organic solvent such as benzene in the presence of a base such as 1,8-diazabicyclo[5.4.0]undec-7-ene.

Further, the compounds represented by the general formula (7) may be prepared by one step by reacting a compound represented by the general formula (5) in an organic solvent such as toluene in the presence of an acid in an amount corresponding to the reaction. Examples of the acid include, for example, p-toluenesulfonic acid, methanesulfonic acid, and the like.

<Preparation Method 3>

[Formula 4]

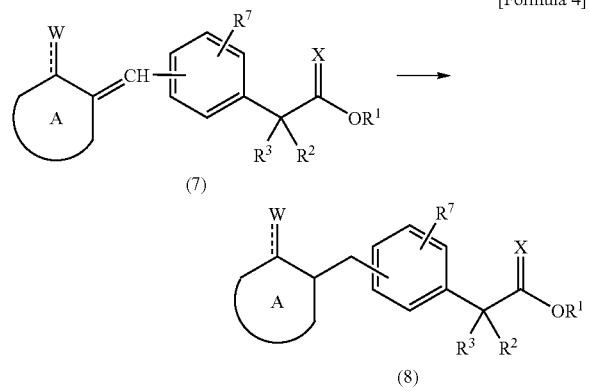

The compounds represented by the general formula (8) can be prepared by reducing a compound represented by the thereof at a temperature of from room temperature to a temperature under reflux by heating, a catalytic hydrogenation reaction using palladium/activated carbon, Raney nickel, Wilkinson complex, or the like as the catalyst, or the like.

<Preparation Method 4>

[Formula 5]

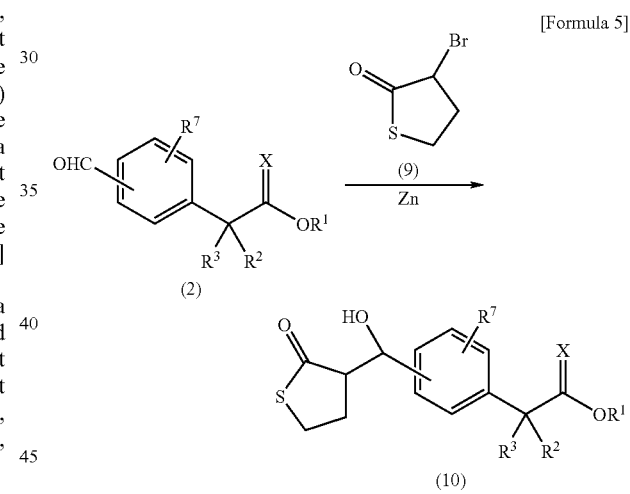

The compounds represented by the general formula (10) can be prepared by, for example, performing the Reformatsky reaction described in, for example, Organic Synthesis, III, 408, 1955 using a compound represented by the general formula (2), and an α-halothiolactone represented by the formula (9).

<Preparation Method 5>

[Formula 6]

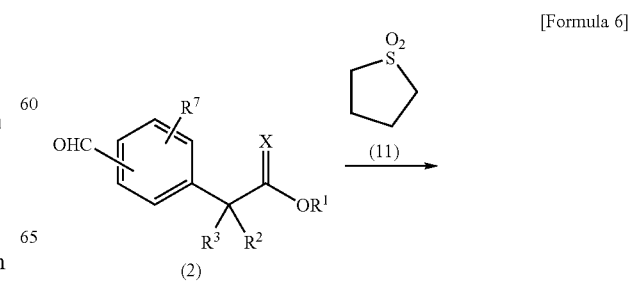

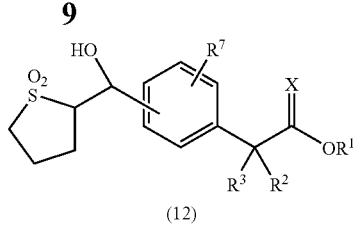

(12)

The compounds represented by the general formula (12) can be prepared by reacting a compound represented by the general formula (2) with a compound represented by the formula (11) in a solvent at a temperature of from −78° C. to room temperature in the presence of a base in an amount corresponding to the reaction. As the solvent, tetrahydrofuran or the like can be used, and examples of the base include n-butyllithium, and the like.

<Preparation Method 6>

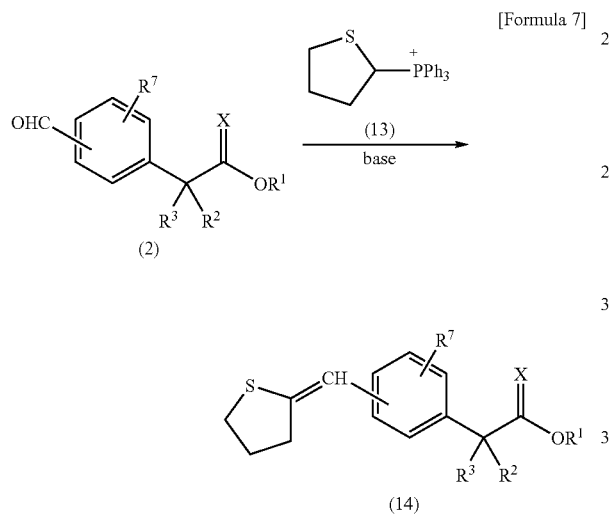

[Formula 7]

The compounds represented by the general formula (14) can be prepared by, for example, performing the Wittig reaction described in, for example, Synthesis, 65, 1975 using a compound represented by the general formula (2), and a phosphonium salt derivative represented by the formula (13).

<Preparation Method 7>

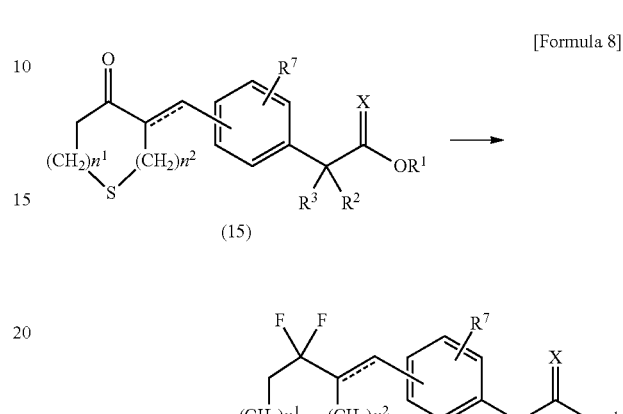

[Formula 8]

The compounds represented by the general formula (16) can be prepared by reacting a compound represented by the general formula (15) with a fluorinating agent in an amount corresponding to the reaction in an organic solvent at a temperature of from room temperature to a temperature under reflux by heating. For example, a target compound can be obtained by performing the reaction without solvent or in an organic solvent such as dichloromethane, chloroform, or trichlorofluoromethane with a fluorinating agent such as diethylaminosulfur trifluoride at a temperature of from room temperature to a temperature under reflux by heating.

<Preparation Method 8>

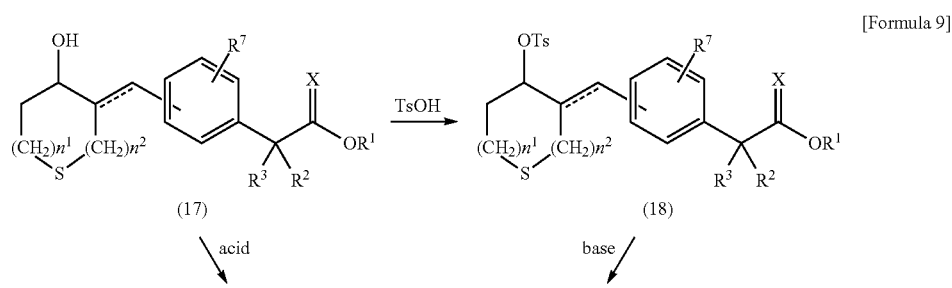

[Formula 9]

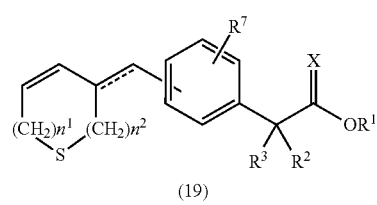

The compounds represented by the general formula (18) may be prepared by reacting a compound represented by the general formula (17) in an organic solvent at a temperature of from room temperature to a temperature under reflux by heating in the presence of p-toluenesulfonic acid (TsOH) in an amount corresponding to the reaction. Examples of the organic solvent include, for example, toluene, benzene, and the like. Further, the compounds represented by the general formula (19) can be obtained by treating a compound represented by the general formula (18) in an organic solvent such as tetrahydrofuran in the presence of a base. Examples of the base include, for example, potassium t-butoxide, and the like. Alternatively, the compounds represented by the general formula (19) can be prepared by reacting a compound represented by the general formula (17) in an organic solvent at a temperature of from room temperature to a temperature under reflux by heating in the presence of an acid in an amount corresponding to the reaction. Examples of the organic solvent include, for example, toluene, benzene, and the like. Examples of the acid include, for example, p-toluenesulfonic acid, and the like.

<Preparation Method 9>

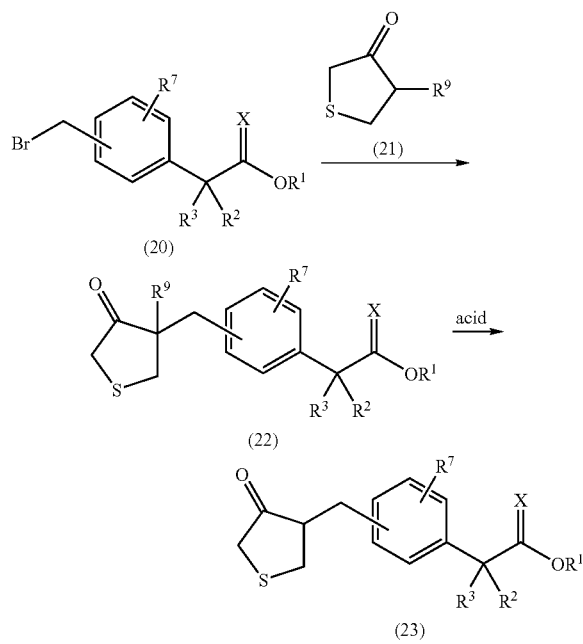

[Formula 10]

(In the Formula, $R^9$ Represents Ethoxycarbonyl Group, or Cyano Group.)

The compounds represented by the general formula (22) can be prepared by reacting a compound represented by the general formula (21), and a benzyl bromide compound represented by the general formula (20) in an organic solvent at a temperature of from room temperature to a temperature under reflux by heating in the presence of a base in an amount corresponding to the reaction. Examples of the organic solvent include, for example, N,N-dimethylformamide, and the like. Examples of the base include, for example, sodium hydride, and the like.

The compounds represented by the general formula (23) can be prepared by reacting a compound represented by the general formula (22) in a polar solvent at a temperature of from room temperature to a temperature under reflux by heating in the presence of an acid in an amount corresponding to the reaction. Examples of the polar solvent include, for example, 1,4-dioxane, water, and the like. Examples of the acid include, for example, sulfuric acid, hydrobromic acid, and the like.

<Preparation Method 10>

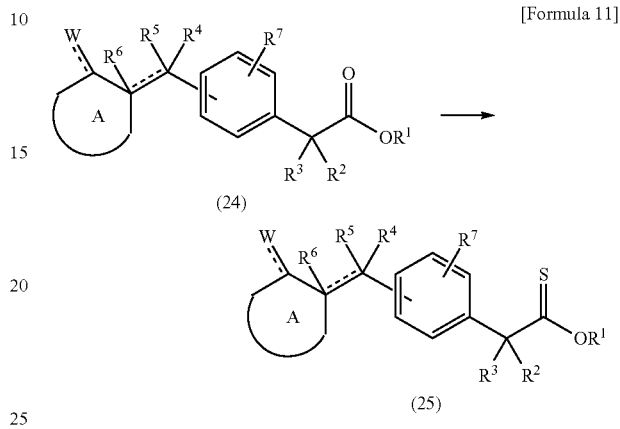

[Formula 11]

The compounds represented by the general formula (25) can be prepared by, for example, subjecting a compound represented by the general formula (24) to a reaction using phosphorus pentasulfide, or the Lawesson's reagent described in Organic Synthesis, 62, 158, 1984, or Synthesis, 831, 1978.

<Preparation Method 11>

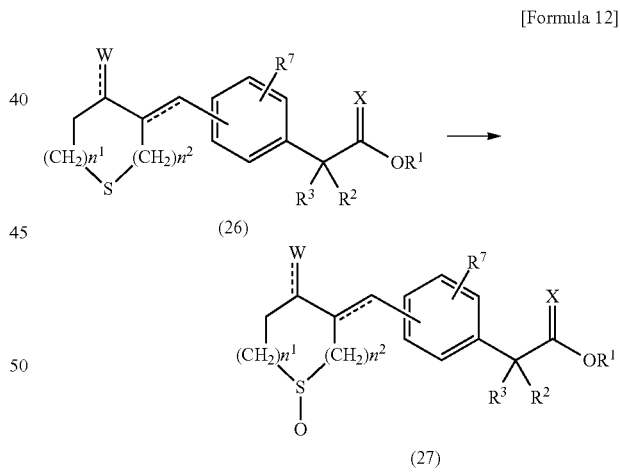

[Formula 12]

The compounds represented by the general formula (27) can be prepared by reacting a compound represented by the general formula (26) in an organic solvent at a temperature of from a temperature under ice cooling to a temperature under reflux by heating in the presence of an oxidizing agent in an amount corresponding to the reaction. Examples of the organic solvent include, for example, dichloromethane, and the like. Examples of the oxidizing agent include, for example, m-chloroperbenzoic acid, hydrogen peroxide, and the like.

<Preparation Method 12>

[Formula 13]

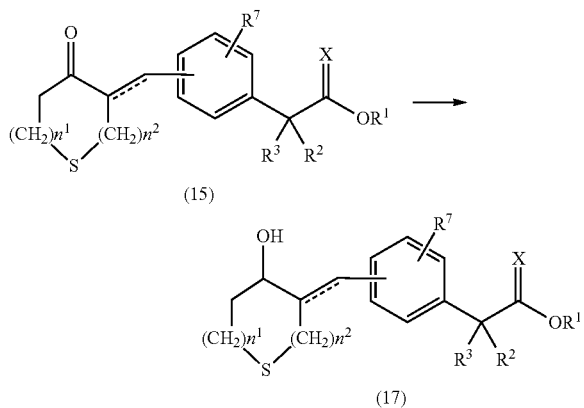

The compounds represented by the general formula (17) can be prepared by reducing a compound represented by the general formula (15) in an organic solvent at a temperature of from a temperature under ice cooling to a temperature under reflux by heating in the presence of a reducing agent in an amount corresponding to the reaction. Examples of the reducing agent include, for example, sodium borohydride, lithium borohydride, lithium aluminum hydride, diisobutylaluminum hydride, and the like. Examples of the solvent include, for example, tetrahydrofuran, dioxane, diethyl ether, dichloromethane, methanol, ethanol, and the like. These solvents may be used as a mixture thereof at a proper mixing ratio.

<Preparation Method 13>

[Formula 14]

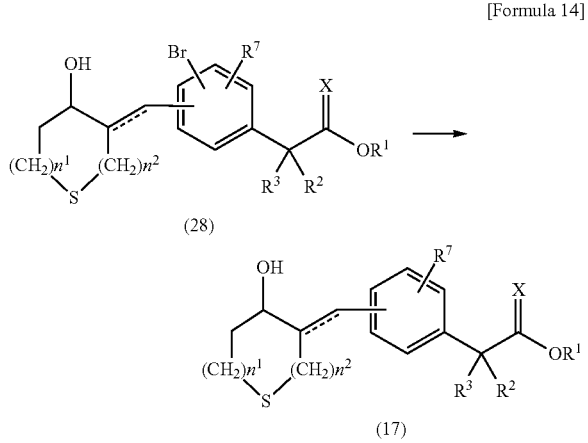

The compounds represented by the general formula (17) can be prepared by reducing a compound represented by the general formula (28) in an organic solvent, water or a mixed solvent of an organic solvent and water in the presence of a base, a hydrogen source and a catalyst in an amount corresponding to the reaction at a temperature of from room temperature to a temperature under reflux by heating. Examples of the organic solvent include, methanol, ethylene glycol dimethyl ether, dimethylformamide, and the like. Examples of the base include triethylamine, pyridine, potassium carbonate, sodium hydroxide, and the like. Examples of the catalyst include tetrakis(triphenylphosphine)palladium, palladium/activated carbon, [1,2-bis(diphenylphosphino) ethane]nickel dichloride/triphenylphosphine, and the like. Examples of the hydrogen source include hydrogen gas, ammonium formate, sodium borohydride, triethylsilane, and the like. Further, palladium chloride, tristriphenylphosphinerhodium chloride, or the like may also be added.

<Preparation Method 14>

Free acids can be obtained by subjecting an ester compound obtained by any of Preparation methods 1 to 13 to an ordinary hydrolysis reaction. For example, the reaction can be performed in an organic solvent at a temperature of from room temperature to a temperature under reflux by heating in the presence of an acid or base in an amount corresponding to the reaction. Examples of the acid include, for example, sulfuric acid, hydrobromic acid, trifluoroacetic acid, and the like, and examples of the base include sodium hydroxide, lithium hydroxide, and the like. When salts of the compounds represented by the general formula (1) are prepared, the compounds can be converted into those in the form of a salt by a treatment in a conventional manner with an acid such as hydrochloric acid, sulfuric acid, nitric acid, hydrobromic acid, acetic acid, oxalic acid, fumaric acid, maleic acid, citric acid, succinic acid, tartaric acid, benzoic acid, methanesulfonic acid, p-toluenesulfonic acid, lactic acid, and butyric acid, a base such as sodium hydroxide, potassium hydroxide, lithium hydroxide, calcium hydroxide, sodium alkoxide, meglumine, tromethamine, olamine, and diolamine, or an amino acid.

The compounds of the present invention represented by the general formula (1) and prepared as described above can be isolated and purified in free form or in the form of salt by ordinary operations such as extraction, concentration, evaporation, crystallization, filtration, recrystallization, various types of chromatography, and the like. Further, isomers such as enantiomers, stereoisomers and position isomers of the compounds of the present invention represented by the general formula (1) can be isolated and purified by, for example, fractionation recrystallization, chiral column method, diastereomer method, or the like in a conventional manner.

For the medicament of the present invention, a substance selected from the group consisting of a compound represented by the general formula (1), a physiologically acceptable salt thereof, and a hydrate and solvate thereof can be used. Although the aforementioned substance, per se, may be used as the medicament of the present invention, a pharmaceutical composition comprising one or more kinds pharmaceutical additives together with the aforementioned substance can be preferably prepared and used. Form of the pharmaceutical composition is not particularly limited, and can be prepared as a pharmaceutical composition in an arbitrary form, for example, a pharmaceutical composition for oral administration such as tablet, pill, capsule, powder, subtilized granule, granule, solution, suspension, and syrup, a pharmaceutical composition for parenteral administration such as injection, patch, cream, ointment, transdermal preparation, inhalant, eye drop, nose drop, ear drop, and suppository, and the like.

Types of the pharmaceutical additives are not particularly limited, and examples include, for example, bases, excipients, lubricants, coating agents, sugar coating agents, wetting agents, binders, disintegrating agents, solvents, solubilizers, dissolving agents, dissolving aids, suspending agents, dispersing agents, emulsifiers, surfactants, isotonic agents, buffering agents, pH modifiers, soothing agents, antiseptics, preservatives, stabilizers, antioxidants, colorants, sweeteners, and the like, but not limited to these examples. Although the pharmaceutical additives may be used independently, two or more kinds of additives in a suitable combination may be used.

Examples of the bases include, for example, kaolin, cacao butter, corn starch, dried aluminum hydroxide gel, crystalline cellulose, methylcellulose, hydroxypropylcellulose, macrogol, and the like. Examples of the excipients include, for example, lactose, sucrose, starch, D-mannitol, corn starch, crystalline cellulose, cellulose derivatives (hydroxypropylcellulose, carmellose calcium, low substituted hydroxypropylcellulose, and the like), light anhydrous silicic acid, calcium hydrogenphosphate, and the like. Examples of the lubricants include, for example, magnesium stearate, calcium stearate, talc, titanium oxide, and the like. Examples of the coating agents include, for example, carmellose calcium, titanium oxide, aluminum stearate, talc, and the like. Examples of the sugar coating agents include, for example, sucrose, lactose, gelatin, paraffin, crystalline cellulose, and the like. Examples of the wetting agents include, for example, glycerol, urea, macrogol, and the like. Examples of the binders include, for example, crystalline cellulose, sucrose, powdered acacia, sodium arginate, carboxymethylethylcellulose, starch, sucrose, purified gelatin, dextrin, methylcellulose, carboxymethylcellulose, carboxymethylcellulose sodium, carboxymethylethylcellulose, hydroxyethylcellulose, hydroxypropylcellulose, hydroxypropylmethylcellulose, pullulan, polyvinyl alcohol, polyvinylpyrrolidone, and the like.

Examples of the disintegrating agent include, for example, sucrose, lactose, starch, agar powder, crospovidone, carboxymethylcellulose, carboxymethyl starch sodium, carmellose, hydroxypropylmethylcellulose, anhydrous citric acid, sodium laurylsulfate, calcium dihydrogenphosphate, and the like. Examples of the solvents include, for example, purified water, water for injection, ethanol, glycerol, propylene glycol, macrogol, sesame oil, corn oil, hydrochloric acid, acetic acid, and the like. Examples of the solubilizers include, glycerol, polyoxyl stearate, polysorbate, macrogol, and the like. Examples of the dissolving agents include, besides those used as the solvents mentioned above, sodium hydroxide, sodium carbonate, meglumine, and the like. Examples of the dissolving aids include, for example, hydrochloric acid, acetic acid, citric acid, sodium citrate, aspartic acid, sodium hydroxide, ethanol, propylene glycol, D-mannitol, sodium benzoate, benzyl benzoate, urea, triethanolamine, polysorbate, polyvinylpyrrolidone, macrogol, and the like. Examples of the suspending agents include, for example, gum arabic, benzalkonium chloride, kaolin, carmellose, sodium laurylsulfate, laurylaminopropionic acid, glyceryl monostearate, polyvinyl alcohol, polyvinylpyrrolidone, carboxymethylcellulose sodium, methylcellulose, hydroxymethylcellulose, hydroxyethylcellulose, hydroxypropylcellulose, and the like.

Examples of the dispersing agents include, for example, sodium citrate, light aluminum oxide, titanium oxide, zinc stearate, polysorbate, macrogol, dextrin, low substituted hydroxypropylcellulose, hydroxypropylcellulose, and the like. Examples of the emulsifiers include, for example, benzalkonium chloride, glycerol, propylene glycol, cetanol, lecithin, lanolin, sodium laurylsulfate, and the like. Examples of the surfactant include, for example, squalane, cetanol, polyoxyethylene cetyl ether, lauromacrogol, and the like. Examples of the isotonic agents include, for example, glucose, D-sorbitol, sodium chloride, glycerol, D-mannitol, and the like. Examples of the buffering agents include, for example, phosphate, acetate, carbonate, citrate buffers, and the like. Examples of the pH modifiers include, for example, inorganic acids such as hydrochloric acid and phosphoric acid, and salts thereof, organic acids such as acetic acid, citric acid, and lactic acid, and salts thereof, and the like. Examples of the soothing agents include, for example, creatinine, benzyl alcohol, and the like. Examples of the antiseptics include, for example, p-oxybenzoic acid esters, chlorobutanol, benzyl alcohol, phenethyl alcohol, dehydroacetic acid, sorbic acid, and the like. Examples of the preservatives include, for example, benzoic acid, p-oxybenzoic acid esters, sorbic acid, and the like. Examples of the stabilizers include, for example, taurine, amino acid, p-oxybenzoic acid esters, benzyl alcohol, crystalline cellulose, macrogol, and the like. Examples of the antioxidants include, for example, sulfite, ascorbic acid, and the like. Examples of the colorants include, edible dyes, β-carotene, riboflavin, and the like. Examples of the sweeteners include aspartame, sucrose, D-sorbitol, maltose, and the like. Examples of aromatics include bitter essence, bitter base, and the like. However, the pharmaceutical additives are not limited to those specifically exemplified above.

The compounds of the present invention represented by the general formula (1) have a superior inhibitory action against $PGE_2$ production as specifically demonstrated by the test examples in the examples mentioned below, and adverse reactions thereof such as gastrointestinal disorders are significantly reduced. Therefore, the aforementioned medicament is useful as a medicament for prophylactic and/or therapeutic treatment of an arbitrary disease resulting from overproduction of prostaglandin, especially overproduction of $PGE_2$. Examples of the disease resulting from overproduction of prostaglandin include, for example, various inflammations, pains, pyrexias, immunologic diseases, infectious diseases, cancers, diabetic complications, obstetric and gynecological diseases, neurodegenerative diseases, cardiovascular diseases, hemopathies, renal diseases, and urologic diseases, and preferred examples include rheumatism, influenza or other virus infections, cold, pain of back or neck, low back pain, headache, toothache, sprain, fibromyositis, neuralgia, synovitis, arthritis including chronic rheumatoid arthritis, degenerative arthritis or osteoarthritis, gout, ankylosing spondilitis, bursitis, burn, inflammation and pain after trauma or surgical or dental treatment, colorectal cancer, breast carcinoma, skin carcinoma, adenoma polyposis, disease and condition relevant to metastatic tumor proliferation, diabetic retinopathy or tumor angiogenesis, smooth muscle contraction, dysmenorrhea, premature labor, asthma, eosinophilic affection, Alzheimer disease, Parkinson's disease, polyglutamine disease, prion disease, amyotrophic lateral sclerosis, bone deficit, gastritis, regional enteritis, ulcerative colitis, anemia, hypoprothrombinemia, hemophilia, renal disease, autoimmune disease, various allergic diseases, heart disorder, cerebrovascular disease, blood coagulation, thrombosis, overactive bladder (OAB, including symptoms of, for example, urinary urgency, pollakiuria, nocturia, and/or urge incontinence), cystitis (including acute simple cystitis, chronic cystitis, complex cystitis, interstitial cystitis, and other various types of cystitis), prostatitis (including acute prostatitis and chronic prostatitis), prostatic hypertrophy, suburethral diverticulitis, urinary tract infection, as well as urinary urgency, pollakiuria, nocturia, and urinary incontinence accompanying diseases other than OAB, and the like, but not limited to these. Among these diseases, inflammations, pains, pyrexias, and urologic diseases are preferred as objective diseases, and OAB (including symptoms of, for example, urinary urgency, pollakiuria, nocturia, and/or urge incontinence), urinary urgency, pollakiuria, nocturia, and urinary incontinence accompanying diseases other than OAB can be mentioned as particularly preferred objective diseases. As diseases other than OAB, diseases resulting from urologic diseases other than OAB or inflammation are preferred, and cystitis (including acute simple cystitis, chronic cystitis, complex cystitis, interstitial cystitis, and other various types of cystitis), prostatitis (including acute prostatitis and chronic prostatitis), prostatic hypertrophy, suburethral diverticulitis, and urinary tract infection are particularly preferred diseases. The medicament of the present invention can be used as a medicament for prophylactic and/or therapeutic treatment of these diseases or syndromes.

Dose of the medicament of the present invention is not particularly limited, and can be suitably chosen depending on patient's symptoms, age and sexuality, the type of an active ingredient, the type of a pharmaceutical composition, the type of a drug used in combination and the like. For example, a daily dose for adults can be usually chosen from the range of 0.1 to 1000 mg, preferably 1 to 500 mg, and the aforementioned dose can be administered once a day or several times as divided portions. Although the medicament of the present invention may be solely administered, the medicament may be administered in combination with other medicaments having the same or different effectiveness. For example, the medicament can be used together with other antiinflammatory agent, antimicrobial agent and the like.

EXAMPLES

The present invention will be more specifically explained with reference to the following examples. However, the scope of the present invention is not limited by the following examples.

The meanings of the abbreviations used in the examples and reference examples are as follows:
$^1$H-NMR: proton nuclear magnetic resonance spectrum, $CDCl_3$: deuterium chloroform, DMSO-$d_6$: deuterium dimethyl sulfoxide, $CD_3OD$: deuterium methanol, Hz: hertz, J: coupling constant, m: multiplet, quint: quintuplet, q: quartet, dt: double triplet, dd: double doublet, ddd: double double doublet, t: triplet, d: doublet, s: singlet, br: broad, Rf: retardation factor, and M: molar concentration. NMR means 270 MHz nuclear magnetic resonance spectrum, and TMS (tetramethylsilane) was used as an internal standard substance.

Example 1 tert-Butyl 2-[4-(4-oxothian-3-ylidenemethyl)phenyl]propionate

To a solution of tert-butyl 2-(4-formylphenyl)propionate (2.0 g), 4-oxothiane (1.2 g) and piperidine (1.0 ml) in toluene (10.0 ml) was added acetic acid (2.0 ml) at room temperature, and then the mixture was refluxed by heating for 3 hours. The reaction mixture was quenched with water, and extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=6/1) to give the title compound (570 mg, 20%).

$^1$H-NMR ($CDCl_3$) δ; 1.40 (9H, s), 1.46 (3H, d, J=7.3 Hz), 2.88-2.95 (2H, m), 2.99-3.07 (2H, m), 3.63 (1H, q, J=7.3 Hz), 3.84 (2H, s), 7.28-7.36 (4H, m), 7.51 (1H, s).

Example 2

2-[4-(4-Oxothian-3-ylidenemethyl)phenyl]propionic Acid tert-Butyl 2-[4-(4-oxothian-3-ylidenemethyl)phenyl]propionate (220 mg) obtained in Example 1 was dissolved in chloroform (2.0 ml), to the solution was added trifluoroacetic acid (2.0 ml), and the mixture was stirred at room temperature for 4 hours. The reaction mixture was quenched with water, and extracted with chloroform. The organic layer was washed with water and saturated brine, and then dried over sodium sulfate. The solvent was evaporated under reduced pressure, and then the residue was purified by silica gel column chromatography (hexane/ethyl acetate=3/2) to give the title compound (160 mg, 87%).

$^1$H-NMR ($CDCl_3$) δ; 1.53 (3H, d, J=7.3 Hz), 2.88-2.95 (2H, m), 2.99-3.07 (2H, m), 3.77 (1H, q, J=7.3 Hz), 3.82 (2H, s), 7.31 (2H, d, J=8.4 Hz), 7.37 (2H, d, J=8.4 Hz), 7.50 (1H, s).

Example 3 tert-Butyl 2-[4-(3-oxothian-2-ylidenemethyl)phenyl]propionate

By using tert-butyl 2-(4-formylphenyl)propionate (500 mg) and 3-oxothiane (500 mg), the title compound (210 mg, 30%) was obtained in the same manner as that of Example 1.

$^1$H-NMR ($CDCl_3$) δ; 1.40 (9H, s), 1.45 (3H, d, J=7.3 Hz), 2.28-2.39 (2H, m), 2.66-2.74 (2H, m), 2.96-3.03 (2H, m), 3.63 (1H, q, J=7.3 Hz), 7.33 (2H, d, J=8.4 Hz), 7.62 (1H, s), 7.63 (2H, d, J=8.4 Hz).

Example 4

2-[4-(3-Oxothian-2-ylidenemethyl)phenyl]propionic Acid tert-Butyl 2-[4-(3-oxothian-2-ylidenemethyl)phenyl]propionate (210 mg) obtained in Example 3 was treated in the same manner as that of Example 2 to give the title compound (80 mg, 46%).

$^1$H-NMR ($CDCl_3$) δ; 1.53 (3H, d, J=7.3 Hz), 2.28-2.38 (2H, m), 2.67-2.73 (2H, m), 2.96-3.03 (2H, m), 3.78 (1H, q, J=7.3 Hz), 7.37 (2H, d, J=8.4 Hz), 7.60 (1H, s), 7.64 (2H, d, J=8.4 Hz).

Example 5

2-[4-(3-Hydroxythian-2-ylidenemethyl)phenyl]propionic Acid

2-[4-(3-Oxothian-2-ylidenemethyl)phenyl]propionic acid (80 mg) obtained in Example 4 was dissolved in methanol (1.0 ml), and to the solution was added sodium borohydride (11 mg) under ice cooling. The mixture was stirred at room temperature for 30 minutes. The reaction mixture was acidified with 10% aqueous citric acid, and extracted with chloroform. The organic layer was washed with water and saturated brine, and then dried over sodium sulfate. The solvent was evaporated under reduced pressure to give the title compound (24 mg, 30%).

$^1$H-NMR ($CDCl_3$) δ; 1.51 (3H, d, J=7.3 Hz), 1.85-2.02 (3H, m), 2.17-2.34 (1H, m), 2.63-2.72 (2H, m), 3.74 (1H, q, J=7.3 Hz), 4.42-4.47 (1H, m), 6.84 (1H, s), 7.30 (2H, d, J=8.4 Hz), 7.48 (2H, d, J=8.4 Hz).

Example 6

Methyl 2-[4-(3-cyano-4-oxothiolan-3-ylmethyl)phenyl]propionate

4-Cyano-3-tetrahydrothiophenone (5.0 g) was dissolved in N,N-dimethylformamide (30 ml), then, sodium hydride (oil, about 60%, 950 mg) was added under ice cooling, and stirred at the same temperature for 30 minutes. Then, to the mixture was added a solution of methyl 2-(4-bromomethylphenyl) propionate (10.1 g) in N,N-dimethylformamide (10.0 ml) under ice cooling, and the reaction mixture was stirred overnight at room temperature. The reaction mixture was quenched with water, and extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=5/1) to give the title compound (5.5 g, 46%).

$^1$H-NMR (CDCl$_3$) δ; 1.50 (3H, d, J=7.3 Hz), 3.01 (1H, d, J=12.4 Hz), 3.11 (1H, d, J=13.8 Hz), 3.20 (1H, d, J=13.8 Hz), 3.23 (1H, d, J=12.4 Hz), 3.41 (1H, d, J=18.1 Hz), 3.55 (1H, d, J=18.1 Hz), 3.68 (3H, s), 3.73 (1H, q, J=7.3 Hz), 7.27-7.31 (4H, m).

Example 7

2-[4-(3-Cyano-4-oxothiolan-3-ylmethyl)phenyl]propionic Acid

Methyl 2-[4-(3-cyano-4-oxothiolan-3-ylmethyl)phenyl]propionate (2.0 g) obtained in Example 6 was dissolved in 1,4-dioxane (14 ml), then, 47% aqueous hydrobromic acid (10.0 ml) was added and stirred overnight at room temperature. The reaction mixture was quenched with water, and extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=1/1) to give the title compound (1.36 g, 78%).

$^1$H-NMR (CDCl$_3$) δ; 1.52 (3H, d, J=7.3 Hz), 3.00 (1H, d, J=12.4 Hz), 3.11 (1H, d, J=13.8 Hz), 3.20 (1H, d, J=13.8 Hz), 3.23 (1H, d, J=12.4 Hz), 3.41 (1H, d, J=18.1 Hz), 3.55 (1H, d, J=18.1 Hz), 3.76 (1H, q, J=7.3 Hz), 7.29 (2H, d, J=8.4 Hz), 7.34 (2H, d, J=8.4 Hz).

Example 8

2-[4-(4-Oxothiolan-3-ylmethyl)phenyl]propionic Acid

2-[4-(3-Cyano-4-oxothiolan-3-ylmethyl)phenyl]propionic acid (1.27 g) obtained in Example 7 was dissolved in 1,4-dioxane (10.0 ml), 30% aqueous sulfuric acid (10.0 ml) was added to the solution and stirred overnight at 110° C. The reaction mixture was quenched with water, and extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=1/1) to give the title compound (550 mg, 50%).

$^1$H-NMR (CDCl$_3$) δ; 1.47 (3H, d, J=7.0 Hz), 2.55-2.65 (1H, m), 267-2.83 (2H, m), 2.97 (1H, dd, J=16.2 Hz, 11.9 Hz), 3.17 (1H, dd, J=14.3 Hz, 3.1 Hz), 3.24 (1H, d, J=17.8 Hz), 3.35 (1H, d, J=17.8 Hz), 3.68 (1H, q, J=7.0 Hz), 7.12 (2H, d, J=8.1 Hz), 7.23 (2H, d, J=8.1 Hz).

Example 9

2-[4-(4-Hydroxythiolan-3-ylmethyl)phenyl]propionic Acid

2-[4-(4-Oxothiolan-3-ylmethyl)phenyl]propionic acid (24 mg) obtained in Example 8 was dissolved in ethanol (1.0 ml), sodium borohydride (9.4 mg) was added stirring on an ice bath, and stirred for 1 hour. The reaction mixture was quenched with 2.0 M aqueous hydrochloric acid, and extracted with ethyl acetate. The aqueous layer was extracted again with ethyl acetate, and the organic layers were combined, and washed with saturated brine. The organic layer was dried over magnesium sulfate, and then the solvent was evaporated under reduced pressure. The residue was purified by silica gel column chromatography (hexane/ethyl acetate/acetic acid=50/50/1) to give the compounds of Example 9-A (colorless crystals, 4.6 mg, 19%) and Example 9-B (colorless oil, 11.6 mg, 48%).

Example 9-A

Rf value: 0.50 (hexane/ethyl acetate/acetic acid=50/50/1)

$^1$H-NMR (CDCl$_3$) δ; 1.44 (3H, d, J=7.3 Hz), 2.30-2.60 (3H, m), 2.70-2.90 (3H, m), 3.05 (1H, dd, J=11.1 Hz, 5.1 Hz), 3.68 (1H, q, J=7.3 Hz), 4.07 (1H, dd, J=9.7 Hz, 4.7 Hz), 7.16 (2H, d, J=8.4 Hz), 7.24 (2H, d, J=8.4 Hz).

Example 9-B

Rf value: 0.45 (hexane/ethyl acetate/acetic acid=50/50/1)

$^1$H-NMR (CDCl$_3$) δ; 1.49 (3H, d, J=7.0 Hz), 2.40-2.65 (3H, m), 2.69 (1H, dd, J=18.4 Hz, 8.1 Hz), 2.81 (1H, dd, J=11.3 Hz, 3.8 Hz), 2.93 (1H, dd, J=10.8 Hz, 5.7 Hz), 3.09 (1H, dd, J=11.3 Hz, 4.9 Hz), 3.70 (1H, q, J=7.0 Hz), 4.18 (1H, dd, J=8.4 Hz, 4.1 Hz), 7.13 (2H, d, J=8.1 Hz), 7.24 (2H, d, J=8.1 Hz).

Example 10

2-[4-(2,3-Dihydrothiophen-3-ylmethyl)phenyl]propionic Acid

2-[4-(4-Hydroxythiolan-3-ylmethyl)phenyl]propionic acid (1.0 g) obtained in Example 9 was dissolved in toluene (30 ml), and p-toluenesulfonic acid (710 mg) was added to the solution and refluxed by heating for 5 hours. After completion of the reaction, the reaction mixture was quenched with water, and the organic layer was separated, and washed with water and saturated brine. Then, the solvent was evaporated under reduced pressure to give a crude product of 2-{4-[4-(4-toluenesulfonyloxy)thiolan-3-ylmethyl]phenyl}propionic acid (700 mg). A part of the product (474 mg) was dissolved in tetrahydrofuran (4.0 ml), and potassium tert-butoxide (506 mg) was added to the solution, and refluxed by heating for 5 hours. After completion of the reaction, the reaction mixture was acidified with 2.0 M aqueous hydrochloric acid under ice cooling, and then extracted with ethyl acetate. The organic layer was washed with water and saturated brine, and then dried over anhydrous magnesium sulfate. The solvent was evaporated under reduced pressure, and the residue was purified by silica gel column chromatography (hexane/ethyl acetate=1/1) to give the title compound (90 mg, 14.4% for 2 steps).

$^1$H-NMR (CDCl$_3$) δ; 1.49 (3H, d, J=7.0 Hz), 2.60-2.83 (2H, m), 2.85-3.02 (1H, q, J=5.3 Hz), 3.08-3.42 (2H, m), 3.71 (1H, q, J=7.0 Hz), 5.54 (1H, dd, J=5.9 Hz, 2.4 Hz), 6.15 (1H, dd, J=5.9 Hz, 1.6 Hz), 7.14 (2H, d, J=8.1 Hz), 7.25 (2H, d, J=8.1 Hz).

Example 11

2-[4-(4-Oxothiolan-3-ylmethyl)phenyl]thiopropionic Acid

2-[4-(4-Oxothiolan-3-ylmethyl)phenyl]propionic acid (300 mg) obtained in Example 8 was dissolved in toluene (3.0 ml), and to the solution was added the Lawesson's reagent (729 mg), and then the reaction mixture was refluxed by heating for 4 hours. After completion of the reaction, the solvent was evaporated under reduced pressure, and the residue was purified by silica gel column chromatography (hexane/ethyl acetate=1/1) to give the title compound (166 mg, 52.4%).

$^1$H-NMR (CDCl$_3$) δ; 1.50 (3H, d, J=7.0 Hz), 2.54-2.66 (1H, m), 2.66-2.82 (2H, m), 2.86-3.06 (1H, m), 3.20 (1H, dd, J=13.5, 2.7 Hz), 3.26 (1H, d, J=17.8 Hz), 3.37 (1H, d, J=17.8 Hz), 3.87 (1H, q, J=7.0 Hz), 7.17 (2H, d, J=8.4 Hz), 7.23 (2H, d, J=8.4 Hz).

Example 12

2-[4-(4-Hydroxythiolan-3-ylmethyl)phenyl]thiopropionic Acid

2-[4-(4-Oxothiolan-3-ylmethyl)phenyl]thiopropionic acid (100 mg) obtained in Example 11 was dissolved in tetrahydrofuran (5.0 ml), and to the solution was added sodium borohydride (16.2 mg) under ice cooling, and then the reaction mixture was stirred at room temperature for 4 hours. After completion of the reaction, to the reaction mixture was added 0.5 M aqueous sulfuric acid, and the reaction mixture was extracted with ethyl acetate, and the organic layer was washed with water and saturated brine, and then dried over anhydrous magnesium sulfate. The solvent was evaporated under reduced pressure, and the residue was purified by silica gel column chromatography (hexane/ethyl acetate=1/1) to give the compounds of Example 12-A (pale brown oil, 16 mg, 15.9%) and Example 12-B (colorless oil, 12 mg, 11.9%).

Example 12-A

Rf value: 0.25 (hexane/ethyl acetate=1/4)
$^1$H-NMR (CDCl$_3$) δ; 1.50 (3H, d, J=7.0 Hz), 2.30 (1H, m), 2.67-3.09 (6H, m), 3.87 (1H, q, J=7.0 Hz), 4.30 (1H, brs), 7.22 (4H, s).

Example 12-B

Rf value: 0.20 (hexane/ethyl acetate=1/4)
$^1$H-NMR (CDCl$_3$) δ; 1.50 (3H, d, J=7.0 Hz), 2.47-3.14 (7H, m), 3.87 (1H, q, J=7.0 Hz), 4.19 (1H, brs), 7.11-7.24 (4H, m).

Example 13 tert-Butyl 2-{4-[3-oxothiolan-(Z)-2-ylidenemethyl]phenyl}propionate

By using tert-butyl 2-(4-formylphenyl)propionate (1.9 g) and 3-oxothiolane (1.24 g), the title compound (570 mg, 22%) was obtained in the same manner as that of Example 1.
$^1$H-NMR (CDCl$_3$) δ; 1.40 (9H, s), 1.46 (3H, d, J=7.3 Hz), 2.80 (2H, t, J=7.3 Hz), 3.25 (2H, t, J=7.3 Hz), 3.64 (1H, q, J=7.3 Hz), 7.36 (2H, d, J=8.4 Hz), 7.44 (1H, s), 7.58 (2H, d, J=8.4 Hz).

Example 14

2-{4-[3-Oxothiolan-(Z)-2-ylidenemethyl]phenyl}propionic Acid

By using tert-butyl 2-{4-[3-oxothiolan-(Z)-2-ylidenemethyl]phenyl}propionate (560 mg) obtained in Example 13, the title compound (180 mg, 48%) was obtained in the same manner as that of Example 2.

$^1$H-NMR (CDCl$_3$) δ; 1.53 (3H, d, J=7.3 Hz), 2.80 (2H, t, J=7.3 Hz), 3.25 (2H, t, J=7.3 Hz), 3.78 (1H, q, J=7.3 Hz), 7.39 (2H, d, J=8.4 Hz), 7.43 (1H, s), 7.59 (2H, d, J=8.4 Hz).

Example 15

Ethyl 2-{4-[3-oxothiolan-(Z)-2-ylidenemethyl]phenyl}propionate

By using ethyl 2-(4-formylphenyl)propionate (10.0 g) and 3-oxothiolane (4.75 g), the title compound (6.8 g, 55%) was obtained in the same manner as that of Example 1.
$^1$H-NMR (CDCl$_3$) δ; 1.21 (3H, t, J=7.3 Hz), 1.51 (3H, d, J=7.3 Hz), 2.80 (2H, t, J=7.3 Hz), 3.25 (2H, t, J=7.3 Hz), 3.73 (1H, q, J=7.3 Hz), 4.06-4.19 (2H, m), 7.37 (2H, d, J=8.4 Hz), 7.43 (1H, s), 7.58 (2H, d, J=8.4 Hz).

Example 16

Ethyl 2-[4-(4-oxothiolan-3-ylidenemethyl)phenyl]propionate

The title compound (0.33 g, 3%) was obtained as a minor component in the same manner as that of Example 15.
$^1$H-NMR (CDCl$_3$) δ; 1.22 (3H, t, J=7.0 Hz), 1.51 (3H, d, J=7.3 Hz), 3.47 (2H, s), 3.75 (1H, q, J=7.3 Hz), 4.04 (2H, d, J=2.4 Hz), 4.07-4.20 (2H, m), 7.38 (2H, d, J=8.4 Hz), 7.45 (1H, s), 7.48 (2H, d, J=8.4 Hz).

Example 17

Ethyl 2-{4-[3-hydroxythiolan-(Z)-2-ylidenemethyl]phenyl}propionate

Ethyl 2-{4-[3-oxothiolan-(Z)-2-ylidenemethyl]phenyl}propionate (6.8 g) obtained in Example 15 was dissolved in a solution (30 ml) of tetrahydrofuran/ethanol (1/2), and to the solution was added sodium borohydride (900 mg) under ice cooling, and the reaction mixture was stirred for 20 minutes. To the reaction mixture was added 10% aqueous citric acid, the solvent was evaporated under reduced pressure, and then the residue was extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=5/2) to give the title compound (5.1 g, 75%).
$^1$H-NMR (CDCl$_3$) δ; 1.20 (3H, t, J=7.3 Hz), 1.49 (3H, d, J=7.3 Hz), 1.72 (1H, d, J=4.3 Hz), 1.98-2.23 (2H, m), 3.12-3.22 (1H, m), 3.36-3.48 (1H, m), 3.70 (1H, q, J=7.3 Hz), 4.02-4.21 (2H, m), 4.84-4.90 (1H, m), 6.69 (1H, s), 7.30 (2H, d, J=8.4 Hz), 7.42 (2H, d, J=8.4 Hz).

Example 18

2-{4-[3-Hydroxythiolan-(Z)-2-ylidenemethyl]phenyl}propionic Acid

Ethyl 2-{4-[3-hydroxythiolan-(Z)-2-ylidenemethyl]phenyl}propionate (5.1 g) obtained in Example 17 was dissolved in ethanol (30 ml), and then to the solution was added 2.0 M aqueous sodium hydroxide (15 ml), and the reaction mixture was stirred for 2.5 hours. The solvent was evaporated under reduced pressure, and then the residue was acidified with 10% aqueous citric acid, and extracted with chloroform. The organic layer was washed with water and saturated brine, and then dried over sodium sulfate. The solvent was evaporated under reduced pressure, and then the residue was purified by silica gel column chromatography (chloroform/methanol=20/1) to give the title compound (4.0 g, 87%).

¹H-NMR (CDCl₃) δ; 1.51 (3H, d, J=7.3 Hz), 1.98-2.22 (2H, m), 3.11-3.21 (1H, m), 3.35-3.47 (1H, m), 3.74 (1H, q, J=7.3 Hz), 4.84-4.89 (1H, m), 6.68 (1H, s), 7.31 (2H, d, J=8.4 Hz), 7.42 (2H, d, J=8.4 Hz).

Example 19

Optical resolution of 2-{4-[3-hydroxythiolan-(Z)-2-ylidenemethyl]phenyl}propionic Acid 2-{4-[3-Hydroxythiolan-(Z)-2-ylidenemethyl]phenyl}propionic acid obtained in Example 18 was separated into 4 isomers by high performance liquid chromatography under the following conditions.
Instrument: Those of Shimadzu Corporation (pump: LC-6AD, column oven: CTO-10ACVP, UV detector: SPD-10AVP)
Column: CHIRALCEL OJ-H (Daicel Chemical Industries, Ltd., Ltd.)
Column temperature: 30° C.
Developing solvent: hexane (containing 0.1% trifluoroacetic acid)/ethanol=72/28 (volume ratio)
Flow rate: 1.0 ml/min
Detection wavelength: 219 nm

Example 19-A (2S,3'R)-2-{4-[3-Hydroxythiolan-(Z)-2-ylidenemethyl]phenyl}propionic Acid Retention time: 13.0 minutes
¹H-NMR (CDCl₃) δ; 1.51 (3H, d, J=7.3 Hz), 1.98-2.22 (2H, m), 3.11-3.21 (1H, m), 3.35-3.47 (1H, m), 3.74 (1H, q, J=7.3 Hz), 4.84-4.89 (1H, m), 6.68 (1H, s), 7.31 (2H, d, J=8.4 Hz), 7.42 (2H, d, J=8.4 Hz).
$[\alpha]_D^{20}$: +45° (c=0.01, EtOH)

Example 19-B (2R,3'R)-2-{4-[3-Hydroxythiolan-(Z)-2-ylidenemethyl]phenyl}propionic Acid Retention time: 14.5 minutes
¹H-NMR (CDCl₃) δ; 1.51 (3H, d, J=7.3 Hz), 1.98-2.22 (2H, m), 3.11-3.21 (1H, m), 3.35-3.47 (1H, m), 3.74 (1H, q, J=7.3 Hz), 4.84-4.89 (1H, m), 6.68 (1H, s), 7.31 (2H, d, J=8.4 Hz), 7.42 (2H, d, J=8.4 Hz).
$[\alpha]_D^{20}$: −55° (c=0.01, EtOH)

Example 19-C (2S,3'S)-2-{4-[3-Hydroxythiolan-(Z)-2-ylidenemethyl]phenyl}propionic Acid Retention time: 17.2 minutes
¹H-NMR (CDCl₃) δ; 1.51 (3H, d, J=7.3 Hz), 1.98-2.22 (2H, m), 3.11-3.21 (1H, m), 3.35-3.47 (1H, m), 3.74 (1H, q, J=7.3 Hz), 4.84-4.89 (1H, m), 6.68 (1H, s), 7.31 (2H, d, J=8.4 Hz), 7.42 (2H, d, J=8.4 Hz).
$[\alpha]_D^{20}$: +54° (c=0.01, EtOH)

Example 19-D (2R,3'S)-2-{4-[3-Hydroxythiolan-(Z)-2-ylidenemethyl]phenyl}propionic Acid Retention time: 19.4 minutes
¹H-NMR (CDCl₃) δ; 1.51 (3H, d, J=7.3 Hz), 1.98-2.22 (2H, m), 3.11-3.21 (1H, m), 3.35-3.47 (1H, m), 3.74 (1H, q, J=7.3 Hz), 4.84-4.89 (1H, m), 6.68 (1H, s), 7.31 (2H, d, J=8.4 Hz), 7.42 (2H, d, J=8.4 Hz).
$[\alpha]_D^{20}$: −46° (C=0.01, EtOH)

Example 20

(2S)-2-[4-(2,5-Dihydrothien-(Z)-2-ylidenemethyl)phenyl]propionic Acid (2S,3'S)-2-{4-[3-Hydroxythiolan-(Z)-2-ylidenemethyl]phenyl}propionic acid (100 mg) obtained in Example 19-C was dissolved in toluene (2.0 ml), and to the solution was added p-toluenesulfonic acid (86.3 mg), and the reaction mixture was stirred for 4 hours under reflux by heating. The solvent was evaporated under reduced pressure, and the residue was purified by silica gel column chromatography (chloroform/methanol=50/1) to give the title compound (12 mg, 12.8%).

¹H-NMR (CDCl₃) δ; 1.50 (3H, d, J=7.3 Hz), 3.72 (1H, q, J=7.3 Hz), 4.13 (2H, s), 6.79 (1H, d, J=3.5 Hz), 6.92 (1H, dd, J=5.1 Hz, 3.5 Hz), 7.58 (1H, d, J=5.1 Hz), 7.16-7.30 (4H, m)

Example 21

Ethyl 2-[4-(4-Hydroxythiolan-3-ylidenemethyl)phenyl]propionate

By using ethyl 2-[4-(4-oxothiolan-3-ylidenemethyl)phenyl]propionate (470 mg) obtained in Example 16, the title compound (380 mg, 80%) was obtained in the same manner as that of Example 17.

¹H-NMR (CDCl₃) δ; 1.21 (3H, t, J=7.3 Hz), 1.49 (3H, d, J=7.3 Hz), 2.21 (1H, d, J=6.8H), 2.78 (1H, dd, J=11.3, 4.6 Hz), 3.03 (1H, dd, J=11.3, 4.6 Hz), 3.63-3.86 (3H, m), 4.02-4.22 (2H, m), 4.79-4.88 (1H, m), 6.67 (1H, s), 7.25 (2H, d, J=8.4 Hz), 7.30 (2H, d, J=8.4 Hz).

Example 22

2-[4-(4-Hydroxythiolan-3-ylidenemethyl)phenyl]propionic Acid

By using ethyl 2-[4-(4-hydroxythiolan-3-ylidenemethyl)phenyl]propionate (380 mg) obtained in Example 21, the title compound (22.3 mg, 6.4%) was obtained in the same manner as that of Example 18.

¹H-NMR (CDCl₃) δ; 1.51 (3H, d, J=7.3 Hz), 2.78 (1H, dd, J=11.3, 4.3 Hz), 3.03 (1H, dd, J=11.3, 4.3 Hz), 3.65-3.80 (3H, m), 4.78-4.83 (1H, m), 6.66 (1H, s), 7.15-7.40 (4H, m).

Example 23

2-[4-(4-Oxothiolan-3-ylidenemethyl)phenyl]propionic Acid

By using Ethyl 2-[4-(4-oxothiolan-3-ylidenemethyl)phenyl]propionate (1.0 g) obtained in Example 16, the title compound (191.7 mg, 20%) was obtained in the same manner as that of Example 8.

$^1$H-NMR (CDCl$_3$) δ; 1.54 (3H, d, J=7.3 Hz), 3.46 (2H, s), 3.80 (1H, q, J=7.3 Hz), 4.03 (2H, d, J=2.4 Hz), 7.38-7.52 (5H, m).

Example 24

Ethyl 2-[4-(3,3-difluorothiolan-2-ylidenemethyl) phenyl]propionate

Ethyl 2-[4-(3-oxothiolan-2-ylidenemethyl)phenyl]propionate (300 mg) obtained in Example 15 was dissolved in diethylaminosulfur trifluoride (3.0 ml), and the solution was stirred at 80° C. for 1 hour. After completion of the reaction, to the reaction mixture was added water, phase separation was performed with ethyl acetate, and the organic layer was dried over sodium sulfate. The solvent was evaporated under reduced pressure, and the residue was purified by silica gel column chromatography (hexane/ethyl acetate=3/1) to give the title compound (43 mg, 13.3%).

$^1$H-NMR (CDCl$_3$) δ; 1.20 (3H, t, J=7.0 Hz), 1.49 (3H, d, J=7.3 Hz), 2.41-2.60 (2H, m), 3.16 (2H, t, J=6.8 Hz), 3.71 (1H, q, J=7.3 Hz), 4.00-4.24 (2H, m), 6.87-6.94 (1H, m), 7.33 (2H, d, J=8.1 Hz), 7.43 (2H, d, J=8.1 Hz).

Example 25

2-[4-(3,3-Difluorothiolan-2-ylidenemethyl)phenyl] propionic Acid

Ethyl 2-[4-(3,3-difluorothiolan-2-ylidenemethyl)phenyl] propionate (43 mg) obtained in Example 24 was dissolved in a solution of ethanol/water (1/1, 1.0 ml), and to the solution was added lithium hydroxide monohydrate (20 mg), and the reaction mixture was stirred at room temperature for 16.5 hours. After completion of the reaction, to the reaction mixture was added 2.0 M aqueous hydrochloric acid, phase separation was performed with ethyl acetate, and the organic layer was dried over sodium sulfate. The solvent was evaporated under reduced pressure, and the residue was purified by silica gel column chromatography (chloroform/methanol=10/1) to give the title compound (33.3 mg, 85.1%).

$^1$H-NMR (CDCl$_3$) δ; 1.51 (3H, d, J=7.3 Hz), 2.39-2.62 (2H, m), 3.16 (2H, t, J=6.8 Hz), 3.75 (1H, q, J=7.3 Hz), 6.87-6.92 (1H, m), 7.34 (2H, d, J=8.1 Hz), 7.44 (2H, d, J=8.1 Hz).

Example 26

2-[4-(3-Oxothiolan-2-ylmethyl)phenyl]propionic Acid

2-[4-(3-Oxothiolan-2-ylidenemethyl)phenyl]propionic acid (500 mg) obtained in Example 14 was dissolved in a mixture of methanol (20 ml)/tetrahydrofuran (10.0 ml)/water (5.0 ml)/acetic acid (1.1 ml), and to the solution was added magnesium (150 mg). The mixture was stirred at room temperature for 2 hours, and then further magnesium (80 mg) was added, and further the solution was stirred for 2 hours. To the reaction mixture was added water and acetic acid, the solution was concentrated under reduced pressure. Saturated brine was added to the residue, and the mixture was extracted with ethyl acetate. The organic layer was dried over magnesium sulfate, and concentrated under reduced pressure, and the resulting residue was purified by silica gel column chromatography (hexane/ethyl acetate=1/1) to give the title compound (132 mg, 26%).

$^1$H-NMR (CDCl$_3$) δ; 1.50 (3H, d, J=7.3 Hz), 2.48-2.95 (5H, m), 3.29 (1H, dd, J=14.0, 4.1 Hz), 3.63 (1H, dd, J=9.2, 4.1 Hz), 3.72 (1H, q, J=7.3 Hz), 7.20 (2H, d, J=8.1 Hz), 7.25 (2H, d, J=8.1 Hz).

Example 27

2-[4-(3-Hydroxythiolan-2-ylmethyl)phenyl]propionic Acid

2-[4-(3-Oxothiolan-2-ylmethyl)phenyl]propionic acid (100 mg) obtained in Example 26 was dissolved in methanol (3.0 ml), and to the solution was added concentrated hydrochloric acid (0.3 ml), and then sodium cyanoborohydride (50 mg) was added. The mixture was stirred overnight, then concentrated under reduced pressure, and extracted with ethyl acetate, and the organic layer was concentrated under reduced pressure. The resulting residue was dissolved in methanol (3.0 ml), and to the solution was added aqueous lithium hydroxide monohydrate (16 mg, 2.0 ml). The mixture was stirred for 30 minutes, then concentrated under reduced pressure, then the residue was acidified with diluted hydrochloric acid, and the mixture was extracted with ethyl acetate. The organic layer was washed with saturated brine, then dried over magnesium sulfate, and concentrated under reduced pressure, and the resulting residue was purified by silica gel column chromatography (hexane/ethyl acetate=1/1) to give isomers of the title compound, compounds of Example 27-A (colorless crystals, 21 mg, 21%) and Example 27-B (colorless oil, 44 mg, 44%).

Example 27-A

Rf value: 0.35 (hexane/ethyl acetate=1/1)

$^1$H-NMR (CDCl$_3$) δ; 1.50 (3H, d, J=7.0 Hz), 1.81-1.98 (1H, m), 2.13-2.25 (1H, m), 2.82-2.98 (2H, m), 3.00-3.13 (2H, m), 3.61 (1H, ddd, J=7.8, 7.8, 3.0 Hz), 3.72 (1H, q, J=7.0 Hz), 4.19-4.25 (1H, m), 7.22-7.26 (4H, m).

Example 27-B

Rf value: 0.30 (hexane/ethyl acetate=1/1)

$^1$H-NMR (CDCl$_3$) δ; 1.50 (3H, d, J=7.0 Hz), 2.06-2.16 (2H, m), 2.75 (1H, dd, J=14.0, 8.1 Hz), 2.88 (1H, dd, J=14.0, 7.3 Hz), 2.91-3.00 (2H, m), 3.61 (1H, ddd, J=8.1, 7.3, 3.2 Hz), 3.72 (1H, q, J=7.0 Hz), 4.19-4.25 (1H, m), 7.17 (2H, d, J=8.1 Hz), 7.26 (2H, d, J=8.1 Hz).

Example 28

Ethyl 4-(3-oxothiolan-2-ylidenemethyl)phenylacetic Acid

From ethyl 4-formylphenylacetate (590 mg), the title compound (950 mg, 78%) was obtained in the same manner as that of Example 1.

$^1$H-NMR (CDCl$_3$) δ; 1.26 (3H, t, J=7.3 Hz), 2.80 (2H, t, J=7.0 Hz), 3.25 (2H, d, J=7.0 Hz), 3.64 (2H, s), 4.16 (2H, q, J=7.3 Hz), 7.35 (2H, d, J=8.4 Hz), 7.44 (1H, s), 7.59 (2H, d, J=8.4 Hz).

Example 29

4-(3-Oxothiolan-2-ylidenemethyl)phenylacetic Acid

From ethyl 4-(3-oxothiolan-2-ylidenemethyl)phenylacetate (200 mg) obtained in Example 28, the title compound (15.5 mg, 9%) was obtained in the same manner as that of Example 25.

¹H-NMR (CD₃OD) δ; 2.79 (2H, t, J=7.0 Hz), 3.25-3.37 (2H, m), 3.64 (2H, s), 7.29-7.50 (3H, m), 7.60 (2H, d, J=8.4 Hz).

Example 30

Ethyl 4-(3-hydroxythiolan-2-ylidenemethyl)phenylacetate

From ethyl 4-(3-oxothiolan-2-ylidenemethyl)phenylacetate (300 mg) obtained in Example 28, the title compound (250 mg, 83%) was obtained in the same manner as that of Example 17.
¹H-NMR (CDCl₃) δ; 1.24 (3H, t, J=7.0 Hz), 1.99-2.22 (2H, m), 3.11-3.21 (1H, m), 3.35-3.47 (1H, m), 3.60 (2H, s), 4.14 (2H, q, J=7.0 Hz), 4.86-4.90 (1H, m), 6.69 (1H, s), 7.28 (2H, d, J=8.1 Hz), 7.42 (2H, d, J=8.1 Hz).

Example 31

4-(3-Hydroxythiolan-2-ylidenemethyl)phenylacetic Acid

From ethyl 4-(3-hydroxythiolan-2-ylidenemethyl)phenylacetate (250 mg) obtained in Example 30, the title compound (72.6 mg, 32%) was obtained in the same manner as that of Example 25.
¹H-NMR (CD₃OD) δ; 1.99-2.10 (2H, m), 3.06-3.16 (1H, m), 3.24-3.40 (1H, m), 3.57 (2H, s), 4.76 (1H, t, J=4.6 Hz), 6.66 (1H, s), 7.24 (2H, d, J=8.4 Hz), 7.40 (2H, d, J=8.4 Hz).

Example 32

Ethyl 2-{4-[hydroxy(2-oxothiolan-3-yl)methyl]phenyl}propionate

3-Bromothiolan-2-one (315 mg) and ethyl 2-(4-formylphenyl)propionate (300 mg) were dissolved in tetrahydrofuran, and to the solution was added zinc (147 mg) and a catalytic amount of iodine, and the reaction mixture was heated until the mixture was refluxed. The reaction mixture was stirred overnight at room temperature, then the solvent was evaporated under reduced pressure, and the residue was purified by silica gel column chromatography (hexane/ethyl acetate=5/1) to give the title compound (106 mg, 20%).
¹H-NMR (CDCl₃) δ; 1.20 (3H, t, J=7.0 Hz), 1.47 (3H, d, J=7.3 Hz), 1.98 (1H, m), 2.31-2.52 (1H, m), 2.72-2.85 (1H, m), 2.87 (1H, br s), 3.10-3.32 (2H, m), 3.69 (1H, q, J=7.3 Hz), 4.00-4.22 (2H, m), 5.33 (1H, d, J=2.2 Hz), 7.18-7.21 (4H, s).

Example 33

2-{4-[Hydroxy(2-oxothiolan-3-yl)methyl]phenyl}propionic Acid

Ethyl 2-{4-[hydroxy(2-oxothiolan-3-yl)methyl]phenyl}propionate (106 mg) obtained in Example 32 was dissolved in 1,4-dioxane (2.0 ml), and to the solution was added 30% aqueous sulfuric acid (2.0 ml), and the solution was stirred overnight at room temperature. After completion of the reaction, to the reaction mixture was added water, and the mixture was extracted with ethyl acetate, and the organic layer was washed with water and saturated brine, and then dried over anhydrous magnesium sulfate. The solvent was evaporated under reduced pressure, and the residue was purified by silica gel column chromatography (chloroform/methanol=10/1) to give the title compound (64 mg, 66%).
¹H-NMR (CDCl₃) δ; 1.49 (3H, d, J=7.0 Hz), 1.96-2.11 (1H, m), 2.39-2.50 (1H, m), 2.72-2.86 (1H, m), 3.10-3.30 (2H, m), 3.71 (1H, dt, J=14.0, 7.0 Hz), 5.32 (1H, d, J=2.4 Hz), 7.29 (4H, s).

Example 34

Ethyl 2-[4-(2-oxothiolan-3-ylidenemethyl)phenyl]propionate

Ethyl 2-{4-[hydroxy(2-oxothiolan-3-yl)methyl]phenyl}propionate (300 mg) obtained in Example 32 was dissolved in toluene (3.0 ml), and to the solution was added p-toluenesulfonic acid (200 mg), and stirred for 1 hour under reflux by heating. The solvent was evaporated under reduced pressure, and the residue was purified by silica gel column chromatography (hexane/ethyl acetate=5/1) to give the title compound (251 mg, 89%).
¹H-NMR (CDCl₃) δ; 1.21 (3H, t, J=7.0 Hz), 1.51 (H, d, J=7.3 Hz), 3.26-3.42 (4H, m), 3.74 (1H, q, J=7.3 Hz), 4.02-4.24 (2H, m), 7.26-7.49 (4H, m).

Example 35

2-[4-(2-Oxothiolan-3-ylidenemethyl)phenyl]propionic Acid

Ethyl 2-[4-(2-oxothiolan-3-ylidenemethyl)phenyl]propionate (124 mg) obtained in Example 34 was dissolved in 1,4-dioxane (4.0 ml), and then to the solution was added 30% aqueous sulfuric acid (4.0 ml). The reaction mixture was stirred at room temperature for 4 days, then added to water, and the mixture was extracted with ethyl acetate. The organic layer was washed with water and saturated brine, and then dried over anhydrous magnesium sulfate. The solvent was evaporated under reduced pressure, and the residue was purified by silica gel column chromatography (chloroform/methanol=10/1) to give the title compound (65 mg, 58%).
¹H-NMR (CDCl₃) δ; 1.53 (3H, d, J=7.3 Hz), 3.20-3.48 (4H, m), 3.78 (1H, q, J=7.3 Hz), 7.20-7.54 (5H, m).

Example 36

Ethyl 2-[4-(thiolan-2-ylidenemethyl)phenyl]propionate (2-Tetrahydrothienyl)triphenylphosphonium chloride (5.8 g) was dissolved in tetrahydrofuran (30 ml), and to the solution was added dropwise a 1.6 M solution of n-butyllithium in hexane (9.5 ml) at −5° C., and then the mixture was stirred at the same temperature for 30 minutes. Then, to the reaction mixture was added dropwise a solution of ethyl 2-(4-formylphenyl)propionate (3.6 g) in tetrahydrofuran (5.0 ml) at −5° C., and the mixture was stirred at room temperature for 2 hours. The reaction mixture was quenched with 10% aqueous citric acid, and then extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=7/1) to give the title compound (2.5 g, 58%).
¹H-NMR (CDCl₃) δ; 1.20 and 1.21 (3H, 2t, J=7.3 Hz), 1.48 (3H, d, J=7.3 Hz), 1.97-2.20 (2H, m), 2.77-2.88 (2H, m), 3.08 and 3.19 (2H, 2t, J=7.3 Hz), 3.68 (1H, q, J=7.3 Hz), 4.02-4.21 (2H, m), 6.40 and 6.46 (1H, 2s), 7.17 and 7.27 (2H, 2d, J=8.4 Hz), 7.24 and 7.38 (2H, 2d, J=8.4 Hz).

Example 37

2-[4-(Thiolan-2-ylidenemethyl)phenyl]propionic Acid

Ethyl 2-[4-(thiolan-2-ylidenemethyl)phenyl]propionate (450 mg) obtained in Example 36 was treated in the same manner as that of Example 18 to give the title compound (390 mg, 96%).

$^1$H-NMR (CDCl$_3$) δ; 1.50 (3H, d, J=7.3 Hz), 1.97-2.18 (2H, m), 2.77-2.87 (2H, m), 3.07 and 3.19 (2H, 2t, J=7.3 Hz), 3.65-3.76 (1H, m), 6.40 and 6.46 (1H, 2s), 7.17 and 7.28 (2H, 2d, J=8.4 Hz), 7.25 and 7.39 (2H, 2d, J=8.4 Hz).

Example 38

Ethyl 2-{4-[(1,1-dioxotetrahydro-1λ$^6$-thiophen-2-yl)hydroxymethyl]phenyl}propionate Tetrahydrothiophene-1,1-dioxide (1.5 g) was dissolved in tetrahydrofuran (10 ml), and to the solution was added dropwise a 1.6 M solution of n-butyllithium in hexane (6.0 ml) at −60° C. The reaction mixture was gradually warmed to 0° C., stirred at the same temperature for 30 minutes, then a solution of ethyl 2-(4-formylphenyl)propionate (1.5 g) in tetrahydrofuran (2.0 ml) was added dropwise at 0° C., and the mixture was stirred at room temperature for 2 days. The reaction mixture was quenched with 10% aqueous citric acid, and then extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=2/1) to give the title compound (800 mg, 39%).

$^1$H-NMR (CDCl$_3$) δ; 1.21 (3H, t, J=7.3 Hz), 1.49 (3H, d, J=7.3 Hz), 1.90-2.10 (2H, m), 2.16-2.41 (2H, m), 2.94-3.08 (1H, m), 3.12-3.26 (2H, m), 3.31 (1H, d, J=3.0 Hz), 3.70 (1H, q, J=7.3 Hz), 4.02-4.22 (2H, m), 5.44-5.50 (1H, m), 7.27-7.36 (4H, m).

Example 39

Ethyl 2-{4-[chloro-(1,1-dioxotetrahydro-1λ$^6$-thiophen-2-yl)methyl]phenyl}propionate Ethyl 2-{4-[(1,1-dioxotetrahydro-1λ$^6$-thiophen-1-yl)hydroxymethyl]phenyl} propionate (400 mg) obtained in Example 38 was dissolved in 1,4-dioxane (5.0 ml), and then to the solution was added thionyl chloride (0.2 ml), and the mixture was stirred at 70° C. overnight. The reaction mixture was quenched with saturated aqueous sodium hydrogencarbonate, and extracted with ethyl acetate. The organic layer was washed with water and saturated brine, and then dried over sodium sulfate. The solvent was evaporated under reduced pressure to give the title compound (420 mg, 99%).

$^1$H-NMR (CDCl$_3$) δ; 1.21 (3H, t, J=7.3 Hz), 1.49 (3H, d, J=7.3 Hz), 2.03-2.36 (3H, m), 2.62-2.75 (1H, m), 3.00-3.14 (1H, m), 3.15-3.28 (1H, m), 3.59-3.76 (2H, m), 4.01-4.21 (2H, m), 5.22 (1H, d, J=8.9 Hz), 7.32 (2H, d, J=8.4 Hz), 7.42 (2H, d, J=8.4 Hz).

Example 40

Ethyl 2-[4-(1,1-dioxotetrahydro-1λ$^6$-thiophen-2-ylidenemethyl)phenyl]propionate Ethyl 2-{4-[chloro-(1,1-dioxotetrahydro-1λ$^6$-thiophen-2-yl)methyl]phenyl} propionate (420 mg) obtained in Example 39 was dissolved in benzene (7.0 ml), and to the solution was added 1,8-diazabicyclo[5.4.0]undec-7-ene (0.45 ml), and the mixture was stirred for 3 hours. The reaction mixture was quenched with water, and extracted with ethyl acetate. The organic layer was washed with water and saturated brine, and then dried over sodium sulfate. The solvent was evaporated under reduced pressure, and then the residue was purified by silica gel column chromatography (hexane/ethyl acetate=3/1) to give the title compound (300 mg, 79%).

$^1$H-NMR (CDCl$_3$) δ; 1.21 (3H, t, J=7.3 Hz), 1.51 (3H, d, J=7.3 Hz), 2.31 (2H, quint, J=7.3 Hz), 3.00-3.12 (4H, m), 3.73 (1H, q, J=7.3 Hz), 4.04-4.22 (2H, m), 7.24 (1H, t, J=2.7 Hz), 7.33-7.42 (4H, m).

Example 41

2-[4-(1,1-Dioxotetrahydro-1λ$^6$-thiophen-2-ylidenemethyl)phenyl]propionic Acid Ethyl 2-[4-(1,1-dioxotetrahydro-1λ$^6$-thiophen-2-ylidenemethyl)phenyl]propionate (300 mg) obtained in Example 40 was treated in the same manner as that of Example 18 to give the title compound (150 mg, 55%).

$^1$H-NMR (CDCl$_3$) δ; 1.53 (3H, d, J=7.3 Hz), 2.31 (2H, quint, J=7.3 Hz), 2.99-3.11 (4H, m), 3.78 (1H, q, J=7.3 Hz), 7.24 (1H, t, J=2.7 Hz), 7.37-7.41 (4H, m).

Example 42

2-[4-(1,1-Dioxotetrahydro-1λ$^6$-thiophen-2-ylmethyl)phenyl]propionic Acid

2-[4-(1,1-Dioxotetrahydro-1λ$^6$-thiophen-2-ylidenemethyl)phenyl]propionic acid (90 mg) obtained in Example 41 was dissolved in methanol (2.0 ml), and to the solution was added 5% palladium/activated carbon (20 mg), and the mixture was stirred for 1 hour under hydrogen flow. The reaction mixture was filtered, and then the solvent was evaporated under reduced pressure. The residue was purified by column chromatography (hexane/ethyl acetate=1/2) to give the title compound (63 mg, 70%).

$^1$H-NMR (CDCl$_3$) δ; 1.51 (3H, d, J=7.3 Hz), 1.72-2.28 (4H, m), 2.65-2.77 (1H, m), 2.97-3.37 (4H, m), 3.73 (1H, q, J=7.3 Hz), 7.18 (2H, d, J=8.1 Hz), 7.28 (2H, d, J=8.1 Hz).

Example 43

(2S,3'S)-2-{4-[3-Hydroxythiolan-(Z)-2-ylidenemethyl]phenyl}propionic Acid Lithium Salt (2S,3'S)-2-{4-[3-Hydroxythiolan-(Z)-2-ylidenemethyl]phenyl}propionic acid (200 mg) obtained in Example 19-C was dissolved in ethanol (5.0 ml) at room temperature, and to the solution was added aqueous lithium hydroxide monohydrate (31.7 mg, 1.0 ml), and the mixture was stirred overnight. The solvent was evaporated under reduced pressure, and the resulting powder was dissolved in water, and extracted with ethyl acetate. Water was evaporated from the aqueous layer under reduced pressure to give the title compound (150.6 mg, 74%).

$^1$H-NMR (DMSO-d$_6$) δ; 1.23 (3H, d, J=7.0 Hz), 1.80-2.09 (2H, m), 3.01-3.30 (3H, m), 4.60-4.68 (1H, m), 6.58 (1H, s), 7.20-7.29 (4H, m).

Example 44

(2S,3'S)-2-{4-[3-Hydroxythiolan-(Z)-2-ylidenemethyl]phenyl}propionic Acid Sodium Salt By using (2S,3'S)-2-{4-[3-hydroxythiolan-(Z)-2-ylidenemethyl]phenyl}propionic acid (200 mg) obtained in Example 19-C and sodium hydroxide (40 mg), the title compound (219.9 mg, 100%) was obtained in the same manner as that of Example 38.

$^1$H-NMR (DMSO-$d_6$) δ; 1.23 (3H, d, J=7.0 Hz), 1.79-2.08 (2H, m), 3.01-3.26 (3H, m), 4.59-4.68 (1H, m), 6.57 (1H, s), 7.18-7.29 (4H, m).

Example 45

(2S,3'S)-2-{4-[3-Hydroxythiolan-(Z)-2-ylidenemethyl]phenyl}propionic Acid 2-aminoethanol Salt (2S,3'S)-2-{4-[3-Hydroxythiolan-(Z)-2-ylidenemethyl]phenyl}propionic acid (500 mg) obtained in Example 19-C was dissolved in ethyl acetate (10 ml) at room temperature, and to the solution was added 2-aminoethanol (116 mg), and then the mixture was refluxed by heating for 1 hour. The reaction mixture was cooled to room temperature, and then crystals were taken by filtration to give the title compound (513.1 mg, 83%).

$^1$H-NMR (DMSO-$d_6$) δ; 1.29 (3H, d, J=7.0 Hz), 1.80-2.10 (2H, m), 2.69 (2H, t, J=5.4 Hz), 3.01-3.24 (2H, m), 3.40-3.50 (3H, m), 4.60-4.70 (1H, m), 6.59 (1H, s), 7.20-7.35 (4H, m).

Example 46

(2S,3'S)-2-{4-[3-Hydroxythiolan-(Z)-2-ylidenemethyl]phenyl}propionic Acid Potassium Salt By using (2S,3'S)-2-{4-[3-Hydroxythiolan-(Z)-2-ylidenemethyl]phenyl}propionic acid (300 mg) obtained in Example 19-C and potassium hydroxide (64 mg), the title compound (350 mg, 100%) was obtained in the same manner as that of Example 38.

$^1$H-NMR (DMSO-$d_6$) δ; 1.22 (3H, d, J=7.3 Hz), 1.79-2.08 (2H, m), 3.01-3.28 (3H, m), 4.64 (1H, t, J=5.4 Hz), 6.57 (1H, s), 7.20-7.30 (4H, m).

Example 47

(2S,3'S)-2-{4-[3-Hydroxythiolan-(Z)-2-ylidenemethyl]phenyl}propionic Acid Calcium Salt (2S,3'S)-2-{4-[3-Hydroxythiolan-(Z)-2-ylidenemethyl]phenyl}propionic acid (300 mg) obtained in Example 19-C was dissolved in ethanol (6.0 ml) at room temperature, and to the solution was added aqueous calcium hydroxide (42.4 mg, 1.5 ml), and the mixture was stirred for 1 hour. The solvent was evaporated under reduced pressure, and the resulting powder was washed with ethyl acetate to give the title compound (308 mg, 94%).

$^1$H-NMR (DMSO-$d_6$) δ; 1.28 (3H, d, J=7.0 Hz), 1.80-2.08 (2H, m), 3.02-3.24 (3H, m), 4.60-4.68 (1H, m), 5.37-5.50 (1H, brs), 6.58 (1H, s), 7.20-7.38 (4H, m).

Example 48

Methyl 2-(5-bromo-4-formyl-2-methoxyphenyl)propionate

To a suspension of lead tetraacetate (16.8 g) in benzene (80 ml) was added a solution of 2-methoxy-4-methylacetophenone (5.35 g) in methanol (8.25 ml), and then boron trifluoride/diethyl ether complex (16.5 ml) was added dropwise to the mixture with stirring under ice cooling, and the mixture was stirred overnight at room temperature. The reaction mixture was quenched with cold water, and extracted with benzene, and the organic layer was washed successively with saturated aqueous sodium hydrogencarbonate, water, and saturated brine, and then dried over sodium sulfate. The solvent was evaporated under reduced pressure, and then the residue was purified by silica gel column chromatography (hexane/ethyl acetate=15/1) to give ethyl 2-methoxy-4-methylphenylacetate (3.22 g).

The resulting ethyl 2-methoxy-4-methylphenylacetate was dissolved in tetrahydrofuran (50 ml), and to the solution was added dropwise a 1.0 M solution of sodium bis(trimethylsilyl)amide in tetrahydrofuran (19 ml) at −70° C., the mixture was stirred at the same temperature for 1 hour, then methyl iodide (3.1 ml) was added dropwise to the mixture, and the mixture was further stirred at −30° C. for 1 hour. The reaction mixture was quenched with 2 M aqueous hydrochloric acid (15 ml), and extracted with ethyl acetate, and the organic layer was washed with water and saturated brine, and then dried over sodium sulfate. The solvent was evaporated under reduced pressure, and then the residue was purified by silica gel column chromatography (hexane/ethyl acetate=7/1) to give methyl 2-(2-methoxy-4-methylphenyl)propionate (2.65 g).

Methyl 2-(2-methoxy-4-methylphenyl)propionate (2.15 g) was dissolved in chlorobenzene (20 ml), and to the solution was added N-bromosuccinimide (4.03 g) and 2,2'-azobisisobutyronitrile (20 mg), and the mixture was stirred at 100° C. for 1 hour. The reaction mixture was left to cool to room temperature, and then filtered, and the filtrate was concentrated. The residue was purified by silica gel column chromatography (hexane/ethyl acetate=6/1) to give methyl 2-(5-bromo-4-bromomethyl-2-methoxyphenyl) propionate (860 mg).

To a solution of 2-nitropropane (210 mg) in methanol (5 ml) was added sodium methoxide (130 mg), and the solution was refluxed by heating for 0.5 hour, and then cooled on ice. To this reaction mixture was added a solution of methyl 2-(5-bromo-4-bromomethyl-2-methoxyphenyl)propionate (860 mg) obtained above in methanol (4 ml), and the mixture was stirred at room temperature for 2 hours. The solvent was evaporated under reduced pressure, and water was added to the residue, and the mixture was extracted with ethyl acetate. The organic layer was washed successively with 1.0 M aqueous hydrochloric acid, water, and saturated brine, and then dried over sodium sulfate. The solvent was evaporated under reduced pressure, and then the residue was purified by column chromatography (hexane/ethyl acetate=7/1) to give the title compound (540 mg).

$^1$H-NMR (CDCl$_3$) δ; 1.48 (3H, d, J=7.3 Hz), 3.67 (3H, s), 3.87 (3H, s), 4.04 (1H, q, J=7.3 Hz), 7.40 (1H, s), 7.48 (1H, s), 10.28 (1H, s).

Example 49

Methyl 2-[5-bromo-2-methoxy-4-(3-oxothiolan-2-ylidenemethyl)phenyl]propionate

By using methyl 2-(5-bromo-4-formyl-2-methoxyphenyl) propionate (540 mg) obtained in Example 48 and 3-oxothiolane (370 mg), the title compound (230 mg, 35%) was obtained in the same manner as that of Example 1.

¹H-NMR (CDCl₃) δ; 1.46 (3H, d, J=7.3 Hz), 2.83 (2H, t, J=7.3 Hz), 3.26 (2H, t, J=7.3 Hz), 3.68 (3H, s), 3.88 (3H, s), 4.00 (1H, q, J=7.3 Hz), 7.32 (1H, s), 7.45 (1H, s), 7.73 (1H, s).

Example 50

Methyl 2-[5-bromo-4-(3-hydroxythiolan-2-ylidenemethyl)-2-methoxyphenyl]propionate Methyl 2-[5-bromo-2-methoxy-4-(3-oxothiolan-2-ylidenemethyl)phenyl]propionate (230 mg) obtained in Example 49 was treated in the same manner as that of Example 17 to give title compound (230 mg, 99%).
¹H-NMR (CDCl₃) δ; 1.44 (3H, d, J=7.3 Hz), 1.77 (1H, d, J=4.3 Hz), 2.01-2.27 (2H, m), 3.11-3.21 (1H, m), 3.36-3.48 (1H, m), 3.67 (3H, s), 3.86 (3H, s), 3.98 (1H, q, J=7.3 Hz), 4.90-4.97 (1H, m), 6.92 (1H, s), 7.27 (1H, s), 7.38 (1H, s).

Example 51

2-[5-Bromo-4-(3-hydroxythiolan-2-ylidenemethyl)-2-methoxyphenyl]propionic Acid

Methyl 2-[5-bromo-4-(3-hydroxythiolan-2-ylidenemethyl)-2-methoxyphenyl]propionate (140 mg) obtained in Example 50 was treated in the same manner as that of Example 18 to give the title compound (110 mg, 78%).
¹H-NMR (CDCl₃) δ; 1.48 (3H, d, J=7.3 Hz), 2.01-2.27 (2H, m), 3.11-3.21 (1H, m), 3.37-3.49 (1H, m), 3.88 (3H, s), 4.03 (1H, q, J=7.3 Hz), 4.90-4.96 (1H, m), 6.92 (1H, s), 7.29 (1H, s), 7.42 (1H, s).

Example 52

Methyl 2-[4-(3-hydroxythiolan-2-ylidenemethyl)-2-methoxyphenyl]propionate

Methyl 2-[5-bromo-4-(3-hydroxythiolan-2-ylidenemethyl)-2-methoxyphenyl]propionate (50 mg) obtained in Example 50 was dissolved in ethylene glycol dimethyl ether (2 ml), and then to the solution was added ammonium formate (25 mg), triethylamine (0.1 ml) and tetrakis(triphenylphosphine)palladium (50 mg). The mixture was stirred overnight at 80° C. in an argon atmosphere. The solvent was evaporated under reduced pressure, and then the residue was purified by silica gel column chromatography (hexane/ethyl acetate=2/1) to give the title compound (30 mg, 72%).
¹H-NMR (CDCl₃) δ; 1.44 (3H, d, J=7.3 Hz), 1.69 (1H, d, J=4.3 Hz), 1.97-2.23 (2H, m), 3.10-3.22 (1H, m), 3.34-3.48 (1H, m), 3.65 (3H, s), 3.86 (3H, s), 4.04 (1H, q, J=7.3 Hz), 4.82-4.90 (1H, m), 6.69 (1H, s), 7.00 (1H, dd, J=8.1, 1.6 Hz), 7.04 (1H, d, J=1.6 Hz), 7.19 (1H, d, J=8.1 Hz).

Example 53

2-[4-(3-Hydroxythiolan-2-ylidenemethyl)-2-methoxyphenyl]propionic Acid

Methyl 2-[4-(3-hydroxythiolan-2-ylidenemethyl)-2-methoxyphenyl]propionate (40 mg) obtained in Example 52 was treated in the same manner as that of Example 18 to give the title compound (27 mg, 71%).
¹H-NMR (CDCl₃) δ; 1.48 (3H, d, J=7.3 Hz), 1.99-2.24 (2H, m), 3.12-3.22 (1H, m), 3.36-3.48 (1H, m), 3.88 (3H, s), 4.07 (1H, q, J=7.3 Hz), 4.84-4.90 (1H, m), 6.69 (1H, s), 7.02 (1H, dd, J=8.1, 1.6 Hz), 7.06 (1H, d, J=1.6 Hz), 7.23 (1H, d, J=8.1 Hz).

Example 54

Methyl 2-(4-formyl-3-nitrophenyl)propionate

By using 4-methyl-3-nitrophenylacetophenone (8.96 g) as a starting material, the title compound (260 mg) was obtained in the same manner as that of Example 48.
¹H-NMR (CDCl₃) δ; 1.56 (3H, d, J=7.3 Hz), 3.71 (3H, s), 3.90 (1H, q, J=7.3 Hz), 7.72 (1H, dd, J=8.1, 1.9 Hz), 7.94 (1H, d, J=8.1 Hz), 8.06 (1H, d, J=1.9 Hz), 10.40 (1H, s).

Example 55

Methyl 2-[3-nitro-4-(3-oxothiolan-2-ylidenemethyl)phenyl]propionate

By using methyl 2-(4-formyl-3-nitrophenyl)propionate (360 mg) obtained in Example 54 and 3-oxothiolane (270 mg), the title compound (180 mg, 37%) was obtained in the same manner as that of Example 1.
¹H-NMR (CDCl₃) δ; 1.57 (3H, d, J=7.3 Hz), 2.84 (2H, t, J=7.3 Hz), 3.25 (2H, t, J=7.3 Hz), 3.70 (3H, s), 3.83 (1H, q, J=7.3 Hz), 7.61 (1H, dd, J=8.1 Hz, 1.9 Hz), 7.70 (1H, s), 7.81 (1H, d, J=8.1 Hz), 7.94 (1H, d, J=1.9 Hz).

Example 56

Methyl 2-[4-(3-hydroxythiolan-2-ylidenemethyl)-3-nitrophenyl]propionate

Methyl 2-[3-nitro-4-(3-oxothiolan-2-ylidenemethyl)phenyl]propionate (180 mg) obtained in Example 55 was treated in the same manner as that of Example 17 to give the title compound (125 mg, 69%).
¹H-NMR (CDCl₃) δ; 1.55 (3H, d, J=7.3 Hz), 1.84 (1H, d, J=4.3 Hz), 2.05-2.25 (2H, m), 3.08-3.19 (1H, m), 3.32-3.44 (1H, m), 3.69 (3H, s), 3.79 (1H, q, J=7.3 Hz), 4.85-4.92 (1H, m), 7.04 (1H, s), 7.54 (1H, dd, J=8.1, 1.9 Hz), 7.79 (1H, d, J=8.1 Hz), 7.88 (1H, d, J=1.9 Hz).

Example 57

2-[4-(3-Hydroxythiolan-2-ylidenemethyl)-3-nitrophenyl]propionic Acid

Methyl 2-[4-(3-hydroxythiolan-2-ylidenemethyl)-3-nitrophenyl]propionate (125 mg) obtained in Example 56 was treated in the same manner as that of Example 18 to give the title compound (110 mg, 92%).
¹H-NMR (CDCl₃) δ; 1.57 (3H, d, J=7.3 Hz), 2.05-2.25 (2H, m), 3.08-3.19 (1H, m), 3.32-3.44 (1H, m), 3.82 (1H, q, J=7.3 Hz), 4.86-4.92 (1H, m), 7.04 (1H, s), 7.56 (1H, dd, J=8.1, 1.9 Hz), 7.79 (1H, d, J=8.1 Hz), 7.90 (1H, d, J=1.9 Hz).

Example 58

Methyl 2-(3-fluoro-4-formylphenyl)propionate

By using 3-fluoro-4-methylacetophenone (5.0 g) as a starting material, the title compound (1.05 g) was obtained in the same manner as that of Example 48.

¹H-NMR (CDCl₃) δ; 1.53 (3H, d, J=7.3 Hz), 3.70 (3H, s), 3.79 (1H, q, J=7.3 Hz), 7.15 (1H, dd, J=11.6, 1.6 Hz), 7.18-7.24 (1H, m), 7.83 (1H, dd, J=7.8, 7.6 Hz), 10.33 (1H, s).

Example 59

Methyl 2-[3-fluoro-4-(3-oxothiolan-2-ylidenemethyl)phenyl]propionate

By using methyl 2-(3-fluoro-4-formylphenyl)propionate (1.05 g) obtained in Example 58 and 3-oxothiolane (1.02 g), the title compound (770 mg, 52%) was obtained in the same manner as that of Example 1.
¹H-NMR (CDCl₃) δ; 1.51 (3H, d, J=7.3 Hz), 2.81 (2H, t, J=7.3 Hz), 3.26 (2H, t, J=7.3 Hz), 3.68 (3H, s), 3.74 (1H, q, J=7.3 Hz), 7.07 (1H, dd, J=11.3, 1.6 Hz), 7.17 (1H, dd, J=8.1, 1.6 Hz), 7.66 (1H, s), 7.72 (1H, dd, J=8.4, 8.1 Hz).

Example 60

Methyl 2-[3-fluoro-4-(3-hydroxythiolan-2-ylidenemethyl)phenyl]propionate

Methyl 2-[3-fluoro-4-(3-oxothiolan-2-ylidenemethyl)phenyl]propionate (200 mg) obtained in Example 59 was treated in the same manner as that of Example 17 to give the title compound (200 mg, 99%).
¹H-NMR (CDCl₃) δ; 1.49 (3H, d, J=7.3 Hz), 1.74 (1H, d, J=3.2 Hz), 2.00-2.24 (2H, m), 3.12-3.22 (1H, m), 3.37-3.49 (1H, m), 3.69 (3H, s), 3.70 (1H, q, J=7.3 Hz), 4.86-4.93 (1H, m), 6.86 (1H, s), 7.01 (1H, dd, J=11.3, 1.6 Hz), 7.10 (1H, dd, J=8.1, 1.6 Hz), 7.64 (1H, dd, J=8.4, 8.1 Hz).

Example 61

2-[3-Fluoro-4-(3-hydroxythiolan-2-ylidenemethyl)phenyl]propionic Acid

Methyl 2-[3-fluoro-4-(3-hydroxythiolan-2-ylidenemethyl)phenyl]propionate (200 mg) obtained in Example 60 was treated in the same manner as that of Example 18 to give the title compound (170 mg, 89%).
¹H-NMR (CDCl₃) δ; 1.51 (3H, d, J=7.3 Hz), 2.00-2.24 (2H, m), 3.12-3.22 (1H, m), 3.36-3.48 (1H, m), 3.73 (1H, q, J=7.3 Hz), 4.87-4.92 (1H, m), 6.85 (1H, s), 7.03 (1H, dd, J=11.3, 1.6 Hz), 7.13 (1H, dd, J=8.1, 1.6 Hz), 7.65 (1H, dd, J=8.4, 8.1 Hz).

Example 62

Methyl 2-(3-chloro-4-formylphenyl)propionate

By using 3-chloro-4-methylacetophenone (2.28 g) as a starting material, the title compound (170 mg) was obtained in the same manner as that of Example 48.
¹H-NMR (CDCl₃) δ; 1.53 (3H, d, J=7.3 Hz), 3.69 (3H, s), 3.76 (1H, q, J=7.3 Hz), 7.32 (1H, dd, J=7.8, 1.6 Hz), 7.41 (1H, d, J=1.6 Hz), 7.89 (1H, d, J=7.8 Hz), 10.44 (1H, s).

Example 63

Methyl 2-[3-chloro-4-(3-oxothiolan-2-ylidenemethyl)phenyl]propionate

By using methyl 2-(3-chloro-4-formylphenyl)propionate (170 mg) obtained in Example 62 and 3-oxothiolane (115 mg), the title compound (50 mg, 21%) was obtained in the same manner as that of Example 1.
¹H-NMR (CDCl₃) δ; 1.51 (3H, d, J=7.3 Hz), 2.82 (2H, t, J=7.3 Hz), 3.25 (2H, t, J=7.3 Hz), 3.68 (3H, s), 3.72 (1H, q, J=7.3 Hz), 7.28 (1H, dd, J=8.1, 1.9 Hz), 7.39 (1H, d, J=1.9 Hz), 7.73 (1H, d, J=8.1 Hz), 7.80 (1H, s).

Example 64

Methyl 2-[3-chloro-4-(3-hydroxythiolan-2-ylidenemethyl)phenyl]propionate

Methyl 2-[3-chloro-4-(3-oxothiolan-2-ylidenemethyl)phenyl]propionate (50 mg) obtained in Example 63 was treated in the same manner as that of Example 17 to give the title compound (40 mg, 80%).
¹H-NMR (CDCl₃) δ; 1.49 (3H, d, J=7.3 Hz), 1.76 (1H, d, J=4.3 Hz), 2.01-2.25 (2H, m), 3.10-3.21 (1H, m), 3.35-3.47 (1H, m), 3.67 (3H, s), 3.68 (1H, q, J=7.3 Hz), 4.88-4.95 (1H, m), 6.98 (1H, s), 7.22 (1H, dd, J=8.1, 1.9 Hz), 7.33 (1H, d, J=1.9 Hz), 7.67 (1H, d, J=8.1 Hz).

Example 65

2-[3-Chloro-4-(3-hydroxythiolan-2-ylidenemethyl)phenyl]propionic Acid

Methyl 2-[3-chloro-4-(3-hydroxythiolan-2-ylidenemethyl)phenyl]propionate (40 mg) obtained in Example 64 was treated in the same manner as that of Example 18 to give the title compound (33 mg, 82%).
¹H-NMR (CDCl₃) δ; 1.51 (3H, d, J=7.3 Hz), 2.01-2.26 (2H, m), 3.09-3.21 (1H, m), 3.35-3.47 (1H, m), 3.71 (1H, q, J=7.3 Hz), 4.88-4.95 (1H, m), 6.97 (1H, s), 7.24 (1H, dd, J=8.1, 1.9 Hz), 7.35 (1H, d, J=1.9 Hz), 7.68 (1H, d, J=8.1 Hz).

Example 66

Methyl 2-(3-formylphenyl)propionate

By using 3'-methylacetophenone (3.0 g) as a starting material, the title compound (720 mg) was obtained in the same manner as that of Example 48.
¹H-NMR (CDCl₃) δ; 1.55 (3H, d, J=7.3 Hz), 3.68 (3H, s), 3.83 (1H, q, J=7.3 Hz), 7.50 (1H, t, J=7.6 Hz), 7.59 (1H, ddd, J=7.6, 1.6, 1.4 Hz), 7.79 (1H, ddd, J=7.6, 1.6, 1.4 Hz), 7.82 (1H, dd, J=1.6, 1.4 Hz), 10.02 (1H, s).

Example 67

Methyl 2-[3-(3-oxothiolan-2-ylidenemethyl)phenyl]propionate

By using methyl 2-(3-formylphenyl)propionate (720 mg) obtained in Example 66 and 3-oxothiolane (580 mg), the title compound (120 mg, 12%) was obtained in the same manner as that of Example 1.
¹H-NMR (CDCl₃) δ; 1.53 (3H, d, J=7.3 Hz), 2.80 (2H, t, J=7.3 Hz), 3.25 (2H, t, J=7.3 Hz), 3.68 (3H, s), 3.77 (1H, q, J=7.3 Hz), 7.28 (1H, d, J=7.6 Hz), 7.39 (1H, t, J=7.6 Hz), 7.44 (1H, s), 7.52 (1H, d, J=7.6 Hz), 7.56 (1H, s).

Example 68

Methyl 2-[3-(3-hydroxythiolan-2-ylidenemethyl)phenyl]propionate

Methyl 2-[3-(3-oxothiolan-2-ylidenemethyl)phenyl]propionate (120 mg) obtained in Example 67 was treated in the same manner as that of Example 17 to give the title compound (50 mg, 41%).

$^1$H-NMR (CDCl$_3$) δ; 1.51 (3H, d, J=7.3 Hz), 1.70 (1H, d, J=4.3 Hz), 1.99-2.24 (2H, m), 3.12-3.22 (1H, m), 3.36-3.48 (1H, m), 3.67 (3H, s), 3.74 (1H, q, J=7.3 Hz), 4.84-4.91 (1H, m), 6.71 (1H, s), 7.14 (1H, ddd, J=7.0, 1.9, 1.6 Hz), 7.28-7.43 (3H, m).

Example 69

2-[3-(3-Hydroxythiolan-2-ylidenemethyl)phenyl]propionic Acid

Methyl 2-[3-(3-hydroxythiolan-2-ylidenemethyl)phenyl]propionate (50 mg) obtained in Example 68 was treated in the same manner as that of Example 18 to give the title compound (32 mg, 67%).

$^1$H-NMR (CDCl$_3$) δ; 1.53 (3H, d, J=7.3 Hz), 1.98-2.23 (2H, m), 3.10-3.21 (1H, m), 3.34-3.47 (1H, m), 3.76 (1H, q, J=7.3 Hz), 4.84-4.90 (1H, m), 6.70 (1H, s), 7.17 (1H, ddd, J=7.0, 1.9, 1.6 Hz), 7.28-7.44 (3H, m).

The structural formulas of the compounds obtained in the examples mentioned above are shown in the tables mentioned below.

TABLE 1-continued

| Example | Chemical formula |
|---|---|
| 10 | |
| 11 | |
| 12-A | |
| 12-B | |
| 13 | |
| 14 | |
| 15 | |
| 16 | |
| 17 | |
| 18 | |
| 19-A | |
| 19-B | |
| 19-C | |
| 19-D | |

TABLE 2

| Example | Chemical formula |
|---|---|
| 20 | |
| 21 | |
| 22 | |
| 23 | |
| 24 | |
| 25 | |
| 26 | |

TABLE 2-continued

| Example | Chemical formula |
|---|---|
| 27-A | |
| 27-B | |
| 28 | |
| 29 | |
| 30 | |
| 31 | |
| 32 | |

TABLE 2-continued

| Example | Chemical formula |
|---|---|
| 33 | (structure: 2-oxo-thiolane with CH(OH) linked to phenyl bearing CH(CH₃)COOH) |
| 34 | (structure: 2-oxo-thiolane with =CH- linked to phenyl bearing CH(CH₃)C(O)OEt) |
| 35 | (structure: 2-oxo-thiolane with =CH- linked to phenyl bearing CH(CH₃)COOH) |
| 36 | (structure: thiolane with =CH- linked to phenyl bearing CH(CH₃)C(O)OEt) |
| 37 | (structure: thiolane with =CH- linked to phenyl bearing CH(CH₃)COOH) |
| 38 | (structure: thiolane-1,1-dioxide with CH(OH) linked to phenyl bearing CH(CH₃)C(O)OEt) |
| 39 | (structure: thiolane-1,1-dioxide with CH(Cl) linked to phenyl bearing CH(CH₃)C(O)OEt) |

TABLE 2-continued

| Example | Chemical formula |
|---|---|
| 40 | (structure: thiolane-1,1-dioxide with =CH- linked to phenyl bearing CH(CH₃)C(O)OEt) |
| 41 | (structure: thiolane-1,1-dioxide with =CH- linked to phenyl bearing CH(CH₃)COOH) |
| 42 | (structure: thiolane-1,1-dioxide with CH₂ linked to phenyl bearing CH(CH₃)COOH) |

TABLE 3

| Example | Chemical formula |
|---|---|
| 43 | (structure: 3-hydroxy-thiolane with =CH- linked to phenyl bearing CH(CH₃)C(O)O⁻ Li⁺) |
| 44 | (structure: 3-hydroxy-thiolane with =CH- linked to phenyl bearing CH(CH₃)C(O)O⁻ Na⁺) |
| 45 | (structure: 3-hydroxy-thiolane with =CH- linked to phenyl bearing CH(CH₃)C(O)O⁻ ⁺H₃N-CH₂CH₂-OH) |
| 46 | (structure: 3-hydroxy-thiolane with =CH- linked to phenyl bearing CH(CH₃)C(O)O⁻ K⁺) |

TABLE 3-continued
| Example | Chemical formula |
|---|---|
| 47 | 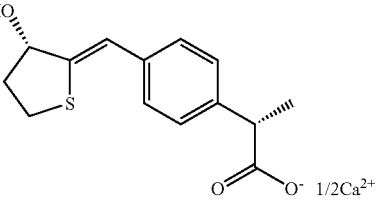 |
| 49 | 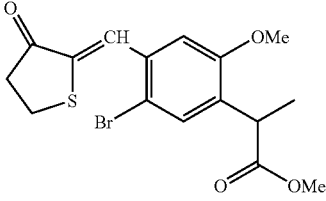 |
| 50 | 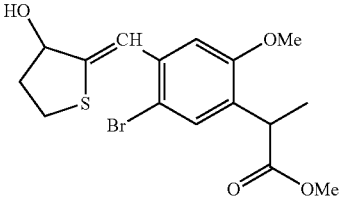 |
| 51 | 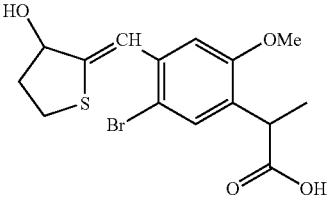 |
| 52 | 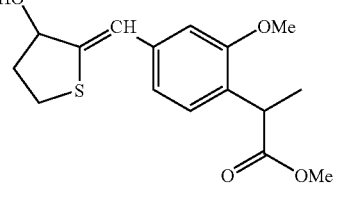 |
| 53 | 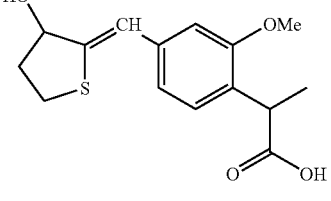 |
| 55 | 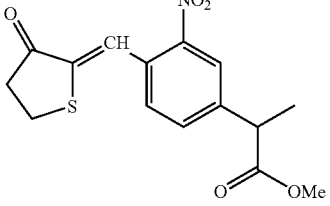 |
| 56 | 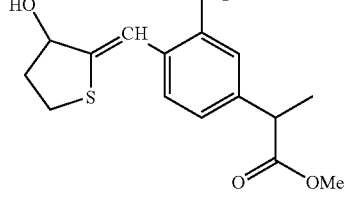 |
| 57 | 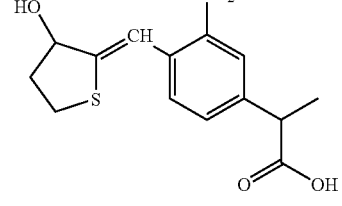 |
| 59 | 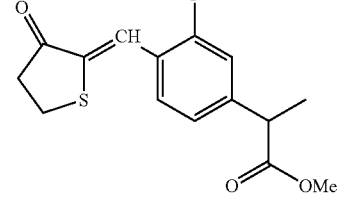 |
| 60 | 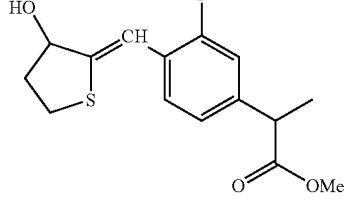 |
| 61 | 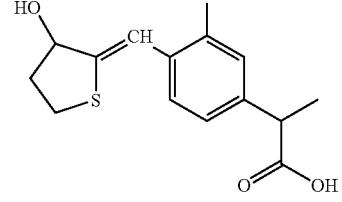 |
| 63 | 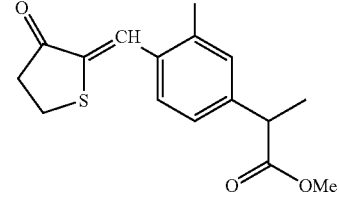 |
| 64 | 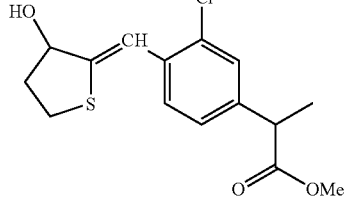 |

TABLE 3-continued

| Example | Chemical formula |
|---|---|
| 65 | (structure: HO-thiolane=CH-phenyl(Cl)-CH(CH₃)-C(=O)-OH) |
| 67 | (structure: O=thiolane=CH-phenyl-CH(CH₃)-C(=O)-OMe) |
| 68 | (structure: HO-thiolane=CH-phenyl-CH(CH₃)-C(=O)-OMe) |
| 69 | (structure: HO-thiolane=CH-phenyl-CH(CH₃)-C(=O)-OH) |

Preparation Example

Tablet

| | |
|---|---|
| Compound of Example 19-C | 5.0 mg |
| Lactose | 50.8 mg (or suitable amount) |
| Corn starch | 24.0 mg |
| Crystalline cellulose | 36.0 mg |
| Hydroxypropylcellulose | 3.6 mg |
| Magnesium stearate | 0.6 mg |
| Total | 120.0 mg |

The aforementioned components are weighed in the ratios of the formulation, and powder for compression is prepared by the wet granulation method. Compression was performed by using the above powder to obtain tablets so that each tablet contains 5 mg of the compound of Example 19-C.

Test Example 1

In Vitro Evaluation Method (Suppressing Action Against $PGE_2$ Production in Human Cultured Cells)

A549 cells were inoculated on a 24-well plate ($10^5$ cells/ml/well), and cultured for 1 day in the Ham's F-12 medium containing 10% fetal bovine serum (FBS). The medium was removed, and the cells were washed with Dulbecco's phosphate buffered saline (PBS), and then cultured for 3 days in the Ham's F-12 medium containing 1 ng/ml of a recombinant human IL-1β and FBS to induce cyclooxygenase 2. After the medium was removed, and the cells were washed with PBS, 0.99 ml of the Ham's F-12 mediums containing a test substance (dissolved in dimethyl sulfoxide at a final concentration of 1% and added) and 0.5 M L-glutathione reduced was added to the cells, and the cells were incubated at 37° C. for 30 minutes in a 5% $CO_2$ incubator. To the culture was added 10 µl of a 0.5 mg/ml solution of arachidonic acid in ethanol (final concentration: 5 µg/ml), and the reaction was performed by incubating the culture at 37° C. and 50 rpm for 30 minutes. After completion of the reaction, the medium was immediately collected, and the $PGE_2$ concentration in the medium was measured by using Prostaglandin $E_2$ Express EIA Kit (Cayman Chemical). Dimethyl sulfoxide not containing the test substance was added to a blank and a control, and ethanol not containing arachidonic acid was added to the blank to perform the reaction. The experiment was performed in duplicate. The suppression rate of the test substance based on the control was calculated by using the following equation.

Suppression rate (100%)=100×[1−($PGE_2$ concentration in medium containing test substance−$PGE_2$ concentration in medium of blank)/($PGE_2$ concentration in medium of control−$PGE_2$ concentration in medium of blank)]

TABLE 4

| $PGE_2$ production suppression rate at 10 µM | |
|---|---|
| Example | Suppression rate (%) |
| 4 | 77.8 |
| 5 | 68.4 |
| 8 | 66.4 |
| 9-A | 34.7 |
| 10 | 69.4 |
| 11 | 49.2 |
| 13 | 48.0 |
| 14 | 98.5 |
| 15 | 36.9 |
| 18 | 99.5 |
| 19-C | 101.4 |
| 19-D | 44.5 |
| 20 | 94.5 |
| 22 | 99.7 |
| 23 | 101.6 |
| 25 | 73.3 |
| 26 | 79.6 |
| 27-A | 40.0 |
| 27-B | 76.3 |
| 29 | 96.8 |
| 31 | 85.9 |
| 35 | 44.0 |
| 37 | 89.7 |
| 53 | 72.8 |
| 57 | 91.6 |
| 61 | 92.8 |
| 65 | 100.9 |
| 69 | 22.8 |
| LXP-2a | 92.0 |

LXP-2a: Active metabolite of Loxoprofen-Na

Test Example 2

In Vivo Evaluation Method

1. Anti-Pollakiuria Effect in Cyclophosphamide (CPA)-Induced Rat Pollakiuria Model To 7-week old male SD rats, 150 mg/kg of CPA was intraperitoneally administered, and the rats were starved for 24 hours, and then used for the test. Thirty minutes after the oral administration of the test substance, physiological saline (30 ml/kg) was orally administered, the rats were put into a metabolism cage for rats, and then frequency of urination was counted for 3 hours. For the counting of the frequency of urination, a weighing dish hung from an FD pickup was disposed at a urine outlet at the lower part of the metabolism cage, and frequency of urination was obtained based on change of urination volume obtained by a polygraph apparatus. To a control (treated with CPA) and an intact control (no treatment), the solvent was orally administered, and frequency of urination was counted in the same manner. Improvement rate of pollakiuria induced by the CPA treatment relative to the control was calculated in accordance with the following equation, and $ED_{50}$ value was further calculated by the probit method based on the improvement rate at each dose.

Improvement rate (%)=(Urination frequency of control−Urination frequency observed with test substance)/(Urination frequency of control−Urination frequency of intact control)×100

TABLE 5

|  | Example 19-C | Loxoprofen-Na |
|---|---|---|
| $ED_{50}$ value (mg/kg) | 0.10 | 1.80 |

2. Gastric Mucosa Injury Induction Action by Single Oral Administration in Rats

7-Week old male SD rats were starved for 24 hours, and then used for the test. Five hours after the oral administration of a test substance, the stomach was extracted, and incised along the greater curvature of stomach, and a stomach specimen was fixed in a neutrally buffered 1% formalin solution. The stomach specimen was observed under a stereoscopic microscope, and when specimen had four or more hemorrhagic sores or ulcers having a major axis of 0.5 mm or larger, the result was judged to be positive. Positive rate at each dose was calculated in accordance with the following equation, and $UD_{50}$ value was calculated by the probit method.

Positive rate (%)=Number of individuals exhibiting positive result for gastric mucosa injury/Number of used animals×100

TABLE 6

|  | Example 19-C | Loxoprofen-Na |
|---|---|---|
| $UD_{30}$ value (mg/kg) | 13.8 | 25.5 |

3. Safety Factor

Safety factor was obtained in accordance with the following equation using the $ED_{50}$ value and $UD_{30}$ value obtained in the tests for the anti-pollakiuria effect in CPA-induced rat pollakiuria model and the gastric mucosa injury induction action by single oral administration in rats, respectively.

Safety factor=$UD_{30}$ value (mg/kg) for gastric mucosa injury induction action by single oral administration in rats/$ED_{50}$ value (mg/kg) for anti-pollakiuria effect in CPA-induced rat pollakiuria model

TABLE 7

|  | Example 19-C | Loxoprofen-Na |
|---|---|---|
| Safety factor | 138 | 14 |

INDUSTRIAL APPLICABILITY

The compounds of the present invention have a potent suppressing action against $PGE_2$ production as shown in Test Example 1, Table 4, and therefore they are useful as therapeutic and/or prophylactic agents for various diseases such as inflammation, pain, pyrexia, immunologic diseases, infectious diseases, cancers, diabetic diseases, obstetric and gynecological diseases, neurodegenerative diseases, hemopathies, renal diseases, and urologic diseases caused by $PGE_2$. Further, they have a remarkable effect on pollakiuria in the test in vivo as shown in Test Example 2, Table 5, and accordingly, they are useful as therapeutic and/or prophylactic agents for OAB as well as for urinary urgency, pollakiuria, nocturia, and urinary incontinence with a disease resulting from inflammation such as cystitis. Furthermore, the compounds of the present invention cause relatively slight gastrointestinal disorders, such as gastric mucosa disorder observed for many of NSAIDs, in comparative consideration of the efficacy as shown in Tables 6 and 7, and therefore they are useful as medicaments having a broad safe dose range.

What is claimed is:

1. A compound represented by the following general formula (I), a salt thereof, or a hydrate or solvate thereof:

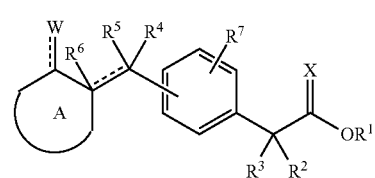

wherein ⚌ represents a single bond, or a double bond; $R^1$ represents hydrogen atom, or a $C_{1-6}$ alkyl group; $R^2$ is a hydrogen atom; $R^3$ is a hydrogen atom, or a $C_{1-6}$ alkyl group; both $R^4$ and $R^5$ are hydrogen atoms, or ⚌ in $>C(R^6)\text{⚌}C(R^5)(R^4)$— is a double bond, or $R^4$ is a hydrogen atom, and $R^5$ is a hydroxy group, or a halogen atom; $R^6$ is hydrogen atom, or cyano group, provided that when ⚌ in $>C(R^6)\text{⚌}C(R^5)(R^4)$— represents a double bond, $R^4$ and $R^6$ do not exist; $R^7$ is one or two of the same or different substituents on the benzene ring selected from the group consisting of hydrogen atom, a halogen atom, nitro group, and a $C_{1-6}$ alkoxyl group; A is a 5-membered or 6-membered non-aromatic heterocyclic ring containing one sulfur atom (the sulfur atom may form oxide); W⚌ is oxo group, two hydrogen atoms, two fluorine atoms, or a combination of hydrogen atom and hydroxy group; and X represents oxygen atom, or sulfur atom.

2. A medicament comprising a substance selected from the compound, a physiologically acceptable salt thereof, and a hydrate or a solvate thereof according to claim 1 as an active ingredient.

3. The medicament according to claim 2, which is in the form of a pharmaceutical composition comprising one or more kinds of pharmaceutical additives together with the active ingredient.

* * * * *